United States Patent
Puri et al.

(10) Patent No.: US 11,925,674 B2
(45) Date of Patent: Mar. 12, 2024

(54) METHODS FOR REGULATING FREE FATTY ACID FLUX USING FAT SPECIFIC PROTEIN 27 (FSP27) COMPOSITIONS

(71) Applicant: Ohio University, Athens, OH (US)

(72) Inventors: Vishwajeet Puri, Athens, OH (US); John Kopchick, Athens, OH (US); Vishva Sharma, Athens, OH (US)

(73) Assignee: Ohio University, Athens, OH (US)

( * ) Notice: Subject to any disclaimer, the term of this patent is extended or adjusted under 35 U.S.C. 154(b) by 0 days.

(21) Appl. No.: 17/873,386

(22) Filed: Jul. 26, 2022

(65) Prior Publication Data

US 2023/0129789 A1 Apr. 27, 2023

Related U.S. Application Data

(62) Division of application No. 16/620,661, filed as application No. PCT/US2018/037443 on Jun. 14, 2018, now Pat. No. 11,433,117.

(60) Provisional application No. 62/520,015, filed on Jun. 15, 2017.

(51) Int. Cl.
| | | |
|---|---|---|
| *A61K 38/17* | (2006.01) | |
| *A61K 9/00* | (2006.01) | |
| *A61P 3/00* | (2006.01) | |
| *A61P 3/06* | (2006.01) | |
| *A61P 3/10* | (2006.01) | |
| *G01N 33/50* | (2006.01) | |

(52) U.S. Cl.
CPC ............ *A61K 38/1709* (2013.01); *A61P 3/00* (2018.01); *A61P 3/06* (2018.01); *A61P 3/10* (2018.01); *A61K 9/0019* (2013.01)

(58) Field of Classification Search
CPC .......... A61K 38/1709; A61P 3/00; A61P 3/06; A61P 3/10
See application file for complete search history.

(56) References Cited

U.S. PATENT DOCUMENTS

2012/0219530 A1    8/2012 Lum et al.

FOREIGN PATENT DOCUMENTS

| EP | 2572730 A1 | 3/2013 |
| WO | 2007039232 A2 | 4/2007 |

OTHER PUBLICATIONS

Yampolsky, Lev Y. and Stoltzfus, Arlin; "The exchangeability of amino acids in proteins." Genetics (2005) 170 p. 1459-1472 (Year: 2005).*

(Continued)

*Primary Examiner* — Julie Ha
*Assistant Examiner* — Kristina M Hellman
(74) *Attorney, Agent, or Firm* — MacMillan, Sobanski & Todd, LLC

(57) ABSTRACT

Methods and FSP27 compositions for treating and/or preventing metabolic disease and conditions associated insulin resistance, obesity, inflammation and dyslipidemia are described.

2 Claims, 19 Drawing Sheets

Specification includes a Sequence Listing.

(56) References Cited

OTHER PUBLICATIONS

Cornier et al., "The metabolic syndrome," Endo. Rev. 29:777-822 (2008) (Year: 2008).*
Dermatitis from Merck Manual, pp. 1-4. Accessed Aug. 30, 2020 (Year: 2020).*
Inflammatory disorders from Merck Manual, pp. 1-4. Accessed Aug. 30, 2020 (Year: 2020).*
Inflammation from Merck Manual, pp. 1-3. Accessed Aug. 30, 2020. (Year: 2020).*
Ebbert et al., "Fat Depots, Free Fatty Acids, and Dyslipidemia," Nutrients 5:498-508 (2013) (Year: 2013).*
Wu et al., "Diabetic dyslipidemia," metabolism clinical and experimental 63:1469-1479 (2014) ( (Year: 2014).*
Yonezawa et al., "which CIDE are you on? A pop ptosis and energy metabolism," Mol. BioSyst. 7:91-100 (2011) (Year: 2011).*
Koonin et al., chapter 2 Evolutionary Concept in Genetics and Genomics, Sequence—Evolution—Function: Computational Approaches in Comparative Genomics. Boston: Kluwer Academic; 2003; NCBI Bookshelf; attached as pdf, 25 pages (Year: 2003).*
Webber et al. (Genes and homology, Current Biology, vol. 14(9):R:332-R333 (May 4, 2004); (Year: 2004).*
Rost, Twilight zone of protein sequence alignments, Protein Engineering, vol. 12(2):85-94 (1999) (Year: 1999).*
Keller et al., "Fat-specific Protein 27 Regulates Storage of Triacylglycerol," J. Biol. Chem. 283:14355-14365 (2008) (Year: 2008).*
UnitProt Accession No. Q96AQ7, accessed May 11, 2023 at URL rest.uniprot.org/uniprotkb/Q96AQ7.txt (Year: 2023).*
Liang et al., "Molecular cloning and characterization of CIDE-3, a novel member of the cell-death-inducing DNA-fragmentation-factor (DFF45)-like effector family," Blochem. J. 370:195-203 (2003) (Year: 2003).*
PCT International Search Report and Written Opinion, Application No. PCT/US2018/037443, dated Sep. 20, 2018.
Grahn et al., "Fat-specific Protein 27 (FSP27) Interacts with Adipose Triglyceride Lipase (ATGL) to Regulate Lipolysis and Insulin Sensitivity in Human Adipocytes", The Journal of Biological Chemistry, 2014, vol. 289, No. 17, pp. 12029-12039.
European Communication Pursuant to Article 94(3) EPC, Application No. 18816687.0, dated Jul. 7, 2022.
Singh et al., "Fat-specific Protein 27 Inhibits Lipolysis by Facilitating the Inhibitory Effect of Transcription Factor Egr1 on Transcription of Adipose Triglyceride Lipase", The Journal of Biological Chemistry, 2014, vol. 289, No. 21, pp. 14481-14487.
Karki, "FSP27 and links to obesity and diabetes mellitus", Current Obesity Reports, 2019, pp. 255-261, Retrieved from the Internet: URL: http://link.springer.com/article/10.1007/s13679-019-00343-3/fulltext.html.
Needleman et al., "A General Method Applicable to the Search for Similarities in the Amino Acid Sequence of Two Protiens", Journal of Molecular Biology, 1970, vol. 48, No. 3, pp. 443-453.
China First Office Action, Application No. 201880047069.6, dated Oct. 20, 2022.

* cited by examiner

METHODS FOR REGULATING FREE FATTY ACID FLUX USING FAT SPECIFIC PROTEIN 27 (FSP27) COMPOSITIONS

CROSS-REFERENCE TO RELATED APPLICATIONS

This application is a divisional application of U.S. application Ser. No. 16/620,661 filed Dec. 9, 2019, now U.S. Pat. No. 11,433,117 issued Sep. 6, 2022, which is a national stage application filed under 35 U.S.C. § 371 of international application PCT/US2018/37443, filed under the authority of the Patent Cooperation Treaty on Jun. 14, 2018, which claims the priority to U.S. Provisional Application Ser. No. 62/520,015 filed Jun. 15, 2017, the entire disclosures of which are expressly incorporated herein by reference.

STATEMENT REGARDING FEDERALLY SPONSORED RESEARCH

This invention was made with government support under RO1DK101711 awarded by The National Institutes of Health. The government has certain rights in this invention.

SEQUENCE LISTING

The instant application contains a Sequence Listing which has been submitted electronically in ASCII format and is hereby incorporated by reference in its entirety. Said ASCII copy, created on Jun. 13, 2018, is named.

BACKGROUND OF THE INVENTION

Obesity has emerged as a major public health problem with currently 69% of the US population and over 2 billion people worldwide characterized as overweight or obese.

The American Medical Association recently formally labeled obesity as a major disease highlighting its critical negative impact on public health. Although much work has centered on obesity prevention, this approach may have come too late, as we are already facing millions of obese adults at high risk for diabetes and other obesity related co-morbidities. The number of extremely obese Americans, in particular, is growing at record pace with no signs of slowing.

Obesity is associated with ectopic fat accumulation, lipotoxicity, adipose tissue dysfunction, and inflammation, which together have been implicated in mechanisms of insulin resistance and type 2 diabetes. It is well established that in obesity there is impaired fat storage and breakdown, which leads to increased circulatory free fatty acids (FFAs; also referred to as unesterified fatty acids). High levels of circulating FFAs are a major risk factor for the lipotoxicity. Ectopic deposition of these FFAs impair insulin signaling in various tissues and organs like liver, muscle and pancreas with the onset of insulin resistance in patients with type 2 diabetes and/or obesity.

Fat specific protein 27 (FSP27) also known as CIDEC (Cell Death Inducing DFFA like Effector C) has recently been identified as being associated with lipid droplets in adipocytes. It is an intracellular protein that has also been shown to be expressed in muscle and liver tissue. FSP27 is strikingly up-regulated during adipogenesis and is highly expressed in adipose tissue. FSP27 depletion in adipocytes causes increased lipolysis, resulting in breakdown of triglycerides into free fatty acids. FSP27 expression in omental fat positively correlates with insulin sensitivity in obese humans. Also, a homozygous nonsense mutation, FSP27 E186X, in a human subject has been shown to be associated with a phenotype of partial lipodystrophy and insulin resistant diabetes.

There is no admission that the background art disclosed in this section legally constitutes prior art.

SUMMARY OF THE INVENTION

In a first broad aspect, described herein are uses of FSP27 compositions. It is now described herein that the exogenous delivery of FSP27 peptides are able to rescue FSP27 dysfunction.

In another broad aspect, described herein are methods of treatment where administering exogenous recombinant FSP27 (rFSP27) as a therapeutic improves insulin signaling in adipocytes and adipose tissue of humans, resulting in decreased insulin resistance.

Such uses include, but are not limited to, increasing levels of FSP27 in a subject by administering exogenous recombinant FSP27 (rFSP27), where the subject is suffering from a metabolic disease and/or other diseases associated with increased free fatty acids and/or lipotoxicity, and conditions associated with these diseases.

In certain embodiments, the metabolic disease and conditions associated with the disease are one or more of insulin resistance, obesity, and dyslipidemia.

In certain embodiments, the other diseases associated with increased free fatty acids and/or lipotoxicity and conditions associated with these diseases are one or more of Type 2 diabetes, fatty liver disease, hypothyroidism, gout, hernia, Pickwickian syndrome, lymph edema, cellulitis, depression, polycystic ovary syndrome, urinary incontinence, chronic renal failure, and erectile dysfunction.

Another use of FSP27 compositions is for reducing visceral obesity, insulin resistance and improving blood glucose levels by administering an effective amount of rFSP27 to improve insulin induced signaling in cells or whole body in a subject in need thereof.

Another use of FSP27 compositions is for modulating lipolysis in adipocytes, by administering rFSP27 to a subject in an amount sufficient to protect that subject from insulin resistance.

Another use of FSP27 compositions is for regulating lipid droplet morphology and optimizing storage and breakdown of fat (lipolysis) in a subject, by administering an effective amount of rFSP27 to a subject in need thereof.

Another use of FSP27 compositions is method for decreasing adipose tissue glycerol lipase (ATGL) expression and lipolysis in a subject in need thereof, by administering an effective amount of rFSP27.

Another use of FSP27 compositions is for protecting adipocyte cells against FFA-induced insulin resistance, by administering an effective amount of rFSP27 to a subject in need thereof.

Another use of FSP27 compositions is for treating pathologies associated with insulin-resistance syndrome, by the administration of an efficient amount of a FSP27 composition to a subject in need thereof. Such pathologies can include, for example, for the treatment of Type 2 diabetes in a subject.

In another broad aspect, described herein are pharmaceutical compositions comprising one or more FSP27 medicaments. FSP27 medicaments may be administered as a pharmaceutically acceptable salt, or as a pegylated composition, or be modified in a pharmaceutically acceptable manner so as to improve the therapeutic properties. FSP27 medicaments may also be administered optionally together with one or more inert carriers and/or diluents. The FSP27 medicament is present in an amount sufficient to treat one or more of: diabetes mellitus, impaired glucose tolerance, hyperglycemia, hypoglycemia, glyceraldehyde-3-phosphate dehydrogenase deficiency, hyperinsulinism/hyperinsulinemia, impaired insulin production, impaired insulin sensitivity, metabolic syndrome, insulin resistance syndrome, obesity, lipidoses, dyslipidemia, fatty liver, lipodystrophy, inflammation and/or other disorders where administration of FSP27 would be efficacious.

In another broad aspect described herein is a method of treating a subject, the method comprising: administering a composition comprising a nucleic acid encoding a FSP27 protein to a subject; and expressing the FSP27 peptide; wherein, the FSP27 protein has an amino acid sequence having greater than about 85% homology to at least one of the FSP27 sequences shown in FIG. 13; the FSP27 protein promoting modulation of lipolysis in adipocytes; and, the subject has a metabolic disease associated with increased free fatty acids and/or lipotoxicity.

In certain embodiments, the FSP27 protein has an amino acid sequence having greater than about 90% homology to the FSP27 sequences.

In certain embodiments, the FSP27 protein has an amino acid sequence having greater than about 95% homology to the FSP27 sequences.

In certain embodiments, the FSP27 protein has an amino acid sequence having greater than about 99% homology to the FSP27 sequences.

In certain embodiments, the FSP27 protein is naturally occurring.

In certain embodiments, the FSP27 protein is a recombinant protein.

In certain embodiments, the FSP27 protein comprises a core FSP27 domain that is associated with TG accumulation, such as aa 120-220.

In certain embodiments, the subject is a human.

In certain embodiments, the subject experiences reduced insulin resistance, obesity and/or dyslipidemia administration of the composition.

In certain embodiments, the nucleic acid encoding the FSP27 protein is operably linked to a constitutive promoter/enhancer, an adipocyte-specific promoter/enhancer, or an inducible promoter/enhancer.

In certain embodiments, the composition comprises a plasmid, the plasmid comprising the nucleic acid encoding the FSP27 protein operably linked to a transcriptional regulatory sequence (promoter/enhancer).

In certain embodiments, the composition comprises a viral vector, the viral vector comprising the nucleic acid encoding the FSP27 protein operably linked to a promoter.

In another broad aspect, described herein is a transgenic mouse expressing human FSP27 in adipose and/or other tissues.

Various objects and advantages of this invention will become apparent to those skilled in the art from the following detailed description of the preferred embodiment, when read in light of the accompanying drawings.

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the U.S. Patent and Trademark Office upon request and payment of the necessary fees.

FIG. 1A. In basal conditions, FSP27 decreases the access of ATGL to its coactivator CGI-58, thereby diminishing lipolysis, as indicated by the dashed downward arrow.

FIG. 1B. When FSP27 is absent in basal conditions, ATGL is free to interact with CGI-58, leading to increased lipolysis, as indicated by solid downward arrow.

FIG. 1C. Upon β-adrenergic stimulation in the presence of FSP27, PKA activation results in phosphorylation of PLIN1 and HSL, causing release of CGI-58 which binds to and stimulates ATGL. Unbound ATGL is translocated to lipid droplet and G0S2 is downregulated to increase ATGL-mediated lipolysis as indicated by the bolded downward arrow.

FIG. 1D. Upon β-adrenergic stimulation in the absence of FSP27, the otherwise FSP27-sequestered-ATGL is now available for CGI-58 binding, resulting in even higher levels of lipolysis, indicated by the more prominent downward arrow.

FIG. 2A. Relative mRNA levels in siRNA-transfected human adipocytes.

FIG. 2B. Immunoblot and quantification of protein expression levels of FSP27 and β-tubulin (loading control) of siRNA-transfected human adipocytes.

FIG. 2C. Biochemical quantification of basal and stimulated lipolysis based on measurement of glycerol release after 2 hours.

FIG. 4A. RNA was extracted from control and siRNA-treated adipocytes, and mRNA levels were measured by quantitative PCR and normalized by GAPDH mRNA.

FIG. 4B. Protein lysates from control and siRNA-treated adipocytes were loaded at 15 μg/lane and probed with antibodies against FSP27, ATGL or β-tubulin.

FIGS. 5A, 5B, 5D, 5F, and 5G. HEK293T cells cultured in 12-well dishes were transfected with the full length (−2979/+21), C→T mutated, or truncated ATGL luciferase promoter constructs, cDNA for eGFP; cDNAs for FSP27 and Egr1 as well as scrambled siRNA and Egr1 siRNA as indicated.

FIG. 5C. Schematic representation of the proximal region of ATGL promoter with the consensus Egr1 binding site. [SEQ ID NO:1].

FIG. 5D. Indicates the synergistic effect between Egr1 and FSP27 with $p<0.05$.

FIG. 5E. HEK293T cells growing in 35 mm dishes were transfected with scrambled or Egr1 siRNA.

FIG. 6A: Insulin stimulated AKT phosphorylation in human adipocytes after siRNA-mediated FSP27 knockdown.

FIG. 6B. Insulin stimulated AKT phosphorylation in human adipocytes in the presence or absence of FSP27-CFP or EGFP (Control).

FIG. 6C. FSP27-HA expression protects adipocytes.

FIG. 6D. 100 μM PA/BSA or FSP27-HA expression had no effect on insulin stimulated AKT activation in adipocytes differentiated from ATGL-KO MEFs.

FIG. 8A. Basal FSP27 was significantly higher in subcutaneous depot.

FIG. 8B. Basal FSP27 protein was measured in 13 paired subcutaneous, and omentum depots.

FIG. 9A. Knockdown of FSP27 in subcutaneous adipose tissue increased rate of glycerol release in the media.

FIG. 9B. siRNA-mediated FSP27 depletion decreased Akt phosphorylation.

FIG. 10A. Treatment of visceral depot with recombinant FSP27 decreased basal lipolysis.

FIG. 10B. Quantification of insulin-stimulated AKT phosphorylation.

FIG. 13 discloses SEQ ID NOs: 2-7, respectively, in order of appearance.

DETAILED DESCRIPTION OF THE PREFERRED EMBODIMENT(S)

Figure 1A:
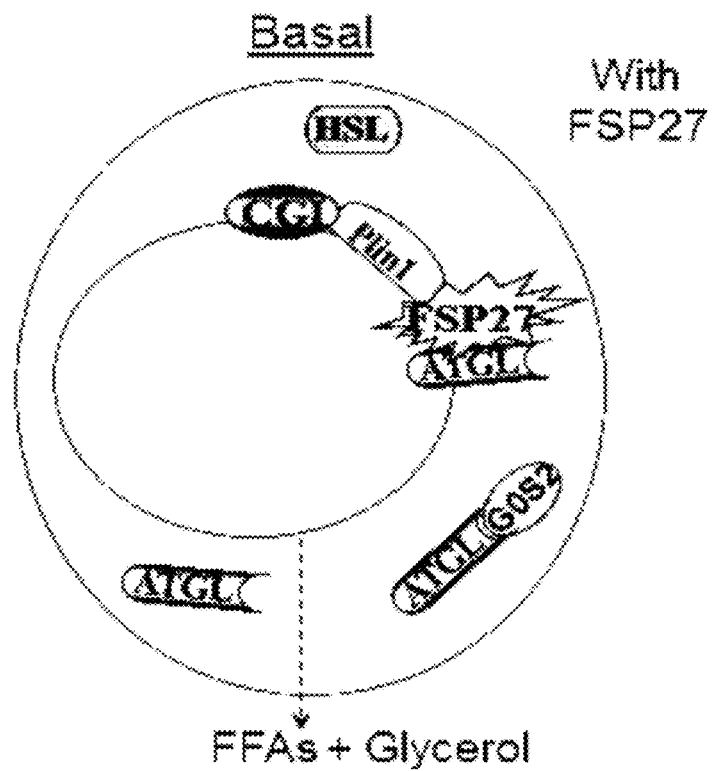
FIGS. 1A-1D: Schematic illustration of a model of FSP27 regulation of lipolysis. A model of FSP27 regulation of lipolysis that is supported by the results described herein. PLIN1 scaffolds FSP27 at the lipid droplet surface where FSP27 interacts with ATGL and decreases lipolysis.

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

Definitions

In order to facilitate review of the various embodiments of the disclosure, the following explanations of specific terms are provided:

FSP27 Compositions/Medicaments: Refers to the FSP27 as shown in the schematic representation of FSP27 and its functional domains in FIG. 12, including any substitutions, deletions, modifications, or mutations thereof. FSP27 Compositions/Medicaments as contemplated herein may also be prepared as recombinant proteins, including the FSP27 sequences shown in FIG. 13.

The FSP27 protein may also be encoded by nucleic acids. As used herein, a "nucleic acid" or "polynucleotide" includes a nucleic acid, an oligonucleotide, a nucleotide, a polynucleotide, and any fragment or variant thereof. The nucleic acid or polynucleotide may be double-stranded, single-stranded, or triple-stranded DNA or RNA (including cDNA), or a DNA-RNA hybrid of genetic or synthetic origin, wherein the nucleic acid contains any combination of deoxyribonucleotides and ribonucleotides and any combination of bases, including, but not limited to, adenine, thymine, cytosine, guanine, uracil, inosine, and xanthine hypoxanthine. The nucleic acid or polynucleotide may be combined with a carbohydrate, lipid, protein, or other materials. Preferably, the nucleic acid encodes FSP27 protein.

The "complement" of a nucleic acid refers, herein, to a nucleic acid molecule which is completely complementary to another nucleic acid, or which will hybridize to the other nucleic acid under conditions of high stringency. High-stringency conditions are known in the art (see e.g., Maniatis et al., Molecular Cloning: A Laboratory Manual, 2nd ed. (Cold Spring Harbor: Cold Spring Harbor Laboratory, 1989) and Ausubel et al., eds., Current Protocols in Molecular Biology (New York, N.Y.: John Wiley & Sons, Inc., 2001)). Stringent conditions are sequence-dependent, and may vary depending upon the circumstances. As used herein, the term "cDNA" refers to an isolated DNA polynucleotide or nucleic acid molecule, or any fragment, derivative, or complement thereof. It may be double-stranded, single-stranded, it may have originated recombinantly or synthetically, and it may represent coding and/or noncoding 5' and/or 3' sequences.

In addition, "complementary" means not only those that are completely complementary to a region of at least 20 continuous nucleotides, but also those that have a nucleotide sequence homology of at least 40% in certain instances, 50% in certain instances, 60% in certain instances, 70% in certain instances, at least 80%, 90%, and 95% or higher. The degree of homology between nucleotide sequences can be determined by an algorithm, BLAST, etc.

As used herein nucleic acids and/or nucleic acid sequences are "homologous" when they are derived, naturally or artificially, from a common ancestral nucleic acid or nucleic acid sequence. Homology is generally inferred from sequence identity between two or more nucleic acids or proteins (or sequences thereof). The precise percentage of identity between sequences that is useful in establishing homology varies with the nucleic acid and protein at issue. Higher levels of sequence identity, e.g., 30%, 40%, 50%, 60%, 70%, 80%, 90%, 95%, 96%, 97%, 98%, or 99% or more can also be used to establish homology. Methods for determining sequence similarity percentages (e.g., BLASTN using default parameters) are generally available. Software for performing BLAST analyses is publicly available through the National Center for Biotechnology Information.

The nucleic acid agent, for example, may be a plasmid. Such a plasmid may comprise a nucleic acid sequence encoding FSP27 or another FSP27-associated protein, although it is to be understood that other types of nucleic acid agents, such as recombinant viral vectors, may also be used for the purposes of the present invention. In one embodiment of the present invention, the nucleic acid (e.g., plasmid) encodes at least one FSP27-associated protein.

The term "plasmid", as used herein, refers generally to circular double-stranded DNA, which is not bound to a chromosome. The DNA, for example, may be a chromosomal or episomal-derived plasmid. The plasmid of the present invention may optionally contain a promoter/enhancer and terminator of transcription, and/or a discrete series of restriction-endonuclease recognition sites, located between the promoter and the terminator. In the plasmid, a polynucleotide insert of interest (e.g., one encoding a FSP27-associated protein) should be operatively linked to an appropriate promoter. The promoter may be its native promoter or a host-derived promoter. The promoter may also be a tissue-specific promoter, such as an adipocyte-specific promoter or other tissue-specific promoter. The promoter may further be a regulatable promoter, which may be turned off when the expression of the gene is no longer desired. Non-limiting examples of promoters for use in the present invention include the actin or albumin promoter and viral promoters. Other suitable promoters will be known to the skilled artisan.

Therapeutic: A generic term that includes both diagnosis and treatment. It will be appreciated that in these methods the "therapy" may be any therapy for treating a disease including, but not limited to, pharmaceutical compositions, gene therapy and biologic therapy such as the administering of antibodies and chemokines. Thus, the methods described herein may be used to evaluate a patient or subject before, during and after therapy, for example, to evaluate the reduction in disease state.

Adjunctive therapy: A treatment used in combination with a primary treatment to improve the effects of the primary treatment.

Clinical outcome: Refers to the health status of a patient following treatment for a disease or disorder or in the absence of treatment. Clinical outcomes include, but are not limited to, an increase in the length of time until death, a decrease in the length of time until death, an increase in the chance of survival, an increase in the risk of death, survival, disease-free survival, chronic disease, metastasis, advanced or aggressive disease, disease recurrence, death, and favorable or poor response to therapy.

Decrease in survival: As used herein, "decrease in survival" refers to a decrease in the length of time before death of a patient, or an increase in the risk of death for the patient.

Patient: As used herein, the term "patient" includes human and non-human animals. The preferred patient for treatment is a human. "Patient," "individual" and "subject" are used interchangeably herein.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop or stops the progression of said disease. "Ameliorating" refers to the reduction in the number or severity of signs or symptoms of a disease.

Poor prognosis: Generally refers to a decrease in survival, or in other words, an increase in risk of death or a decrease in the time until death. Poor prognosis can also refer to an increase in severity of the disease, such as an increase in spread (metastasis) of the cancer to other tissues and/or organs.

Screening: As used herein, "screening" refers to the process used to evaluate and identify candidate agents that affect such disease.

Comprising, comprises and comprised of: As used herein are synonymous with "including", "includes" or "containing", "contains", and are inclusive or open-ended and do not exclude additional, non-recited members, elements or method steps. The terms "comprising", "comprises" and "comprised of" also include the term "consisting of".

About: As used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

And/or: When used in a list of two or more items, means that any one of the listed items can be employed by itself or any combination of two or more of the listed items can be employed. For example, if a list is described as comprising group A, B, and/or C, the list can comprise A alone; B alone; C alone; A and B in combination; A and C in combination, B and C in combination; or A, B, and C in combination.

Metabolic diseases: As used herein means any disease caused by an abnormal metabolic process that may be congenital, resulting from an inherited abnormality, or acquired, resulting from organ or system dysfunction or failure.

General Description

Figure 12:
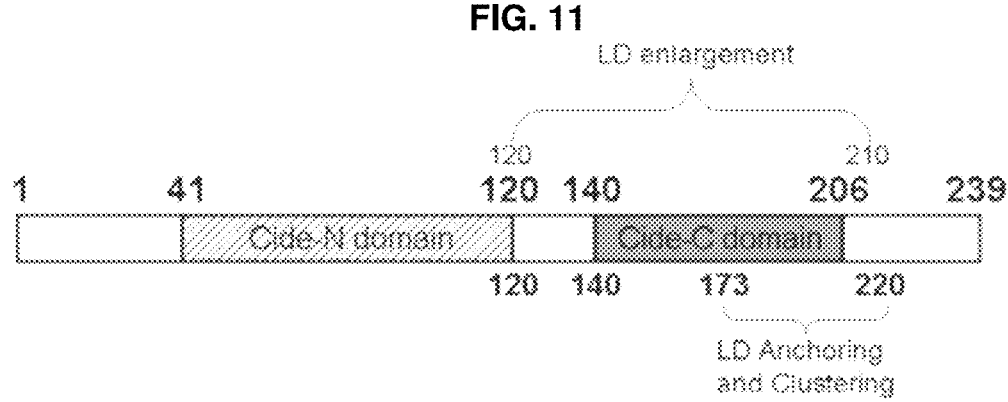
FIG. 12: Schematic representation of FSP27 and its functional domains: CIDE-N and CIDE-C.

Lipotoxicity due to excess adipose tissue lipolysis contributes to insulin-resistance. Fat Specific Protein (FSP27) is a key regulator of lipolysis in adipocytes. Lipotoxicity can exist in muscle, liver, pancreas and other organs. FIG. 12 provides a schematic representation of FSP27 and its functional domains.

FSP27 is a lipid droplet associated protein that regulates fatty acid homeostasis in adipocytes, and its expression is inversely associated with insulin sensitivity in obese humans. Human genetic FSP27 mutations are associated with lipodystrophy, hypertriglyceridemia, and insulin-resistance and inactivating mutations of FSP27 in humans leads to increased lipolysis. In addition, adipose-specific disruption of FSP27 causes insulin resistance in high fat fed mice.

Lipolysis in the Pathogenesis of Insulin Resistance.

Lipolysis is a catabolic branch of the fatty acid (FA) cycle that provides FAs in times of metabolic need. FAs are essential substrates for energy production and the synthesis of most lipids. Despite their fundamental physiological importance, an oversupply of FAs is highly detrimental. Increased free fatty acids (FFAs) cause lipotoxicity which disrupt the integrity of membranes, alters cellular acid-base homeostasis, and elicits the generation of harmful bioactive lipids. These effects, in turn, impair membrane function and induce endoplasmic reticulum (ER) stress, mitochondrial dysfunction, inflammation, cell death, and insulin resistance. Adipose tissue regulates the balance of FA esterification and triglyceride (TG) lipolysis, thus playing a central role in regulating whole body metabolism and glucose homeostasis. High concentrations of circulating FFAs and TG, observed in both obesity and lipodystrophy, are believed to cause insulin resistance and decreased glucose tolerance.

FSP27 Regulates Lipid Droplet Morphology and Lipolysis:

The FSP27 protein associates with lipid droplets and regulates FA homeostasis in adipocytes. FSP27 regulates lipid droplet dynamics and lipolysis in adipocytes through regulation of the catalytic capacity as well as transcription of adipose tissue glycerol lipase, ATGL, the rate-limiting enzyme in lipolysis. FSP27 levels are inversely associated with insulin sensitivity in obese humans, and mutation of FSP27 in humans leads to increased lipolysis. In addition, adipose-specific disruption of FSP27 causes insulin resistance in high fat fed mice.

Described herein is a previously unrecognized role of FSP27 in the regulation of insulin signaling to protect against insulin resistance and Type 2 diabetes. While metabolic regulation of FSP27 has been essentially characterized exclusively in adipocytes, the data herein show that FSP27 is down-regulated particularly in association with visceral/central obesity. Perturbations in FSP27 may promote conditions that elevate FFAs, which cause or promote insulin resistance. However, lipid storage/breakdown is generally not viewed as a primary function of other cell types, thus FSP27 may govern cellular responses by mechanisms beyond regulation of lipid metabolism.

Moreover, at the local adipose tissue level, capillary rarefaction and impaired perfusion have been linked to adipose tissue pseudohypoxia and metabolic dysregulation. FSP27 is down-regulated in human visceral fat and is associated with insulin resistance.

Also described herein are mouse models that are adipose specific transgenic mice expressing human FSP27. These mice are useful to examine the relative contribution of adipose in regulating insulin resistance and/or Type 2 diabetes.

FS-IVGTT

Fasting subjects are studied in the morning in the general clinical research center (GCRC). Any oral diabetic medication is held 48 hrs prior to testing. Two intravenous forearm catheters are placed in each arm (one for sampling and one for infusion). Baseline blood samples are collected at t=−15 min and t=−5 min) for measurement of glucose and insulin. A bolus of 300 mg/kg glucose in 25% glucose/saline infusion over 1 minute is given. At t=20 min, a bolus of 0.05 units/kg of regular insulin intravenously which improves accuracy of the FS-IVGTT in diabetic subjects is given. Blood is collected for insulin and glucose at t=2, 3, 4, 5, 6, 8, 10, 14, 16, 19, 22, 25, 30, 40, 50, 60, 70, 90, 110, 130, 150, 170, and 180 minutes. The insulin sensitivity index (SI) and disposition index (DI) are calculated using the MINMOD software based on the Bergman model. These data collected within 1 week of the planned surgery.

Quantitative Real-Time PCR and Western Blot Analyses

Using Quantitative real-time PCR, fat tissue expression of specific mediators relevant to insulin signaling, FSP27, and inflammation (which will initially consist of: TNFα, IL-6, IL-1β, MCP-1, CD68, FSP27, IRS-1, PI3-K, Akt, PTEN) are examined.

FSP27 is associated with lipid droplets and functions primarily as a regulator of lipid droplet morphology and lipolysis in adipocytes. Visceral adipose tissue showed lower FSP27 expression as compared to subcutaneous depots (see FIGS. 9A-9B).

FSP27 Prevents the Interaction of ATGL with its Activator, CGI-58, Leading to a Decreased Lipolysis in Human Adipocytes.

Lipolysis of TGs to FAs and glycerol requires three consecutive steps that involve three different enzymes, Adipose tissue glycerol lipase (ATGL; also called desnutrin and PNPLA2), Hormone sensitive lipase (HSL), and Monoacylglycerol lipase (MGL). ATGL is the rate-limiting enzyme for lipolysis in adipocytes which catalyzes the first step of hydrolysis of TG to diacyl glycerol (DG).

FSP27 regulates lipolysis in adipocytes through regulation of the catalytic capacity as well as transcription of the adipose tissue glycerol lipase (ATGL) gene. The activity of ATGL depends upon its interaction with its activator CGI-58. As shown in FIGS. 1A-1D, FSP27 interacts with ATGL at lipid droplet surface and inhibits its interaction with the activator CGI-58, thus preventing the activation of ATGL to regulate lipolysis under both basal and stimulated conditions.

FIGS. 1A-1D provide a schematic illustration of a model of FSP27 regulation of lipolysis. FIG. 1A illustrates that, in basal conditions, FSP27 decreases the access of ATGL to its coactivator CGI-58, thereby diminishing lipolysis, as indicated by the dashed downward arrow.

Figure 1B:
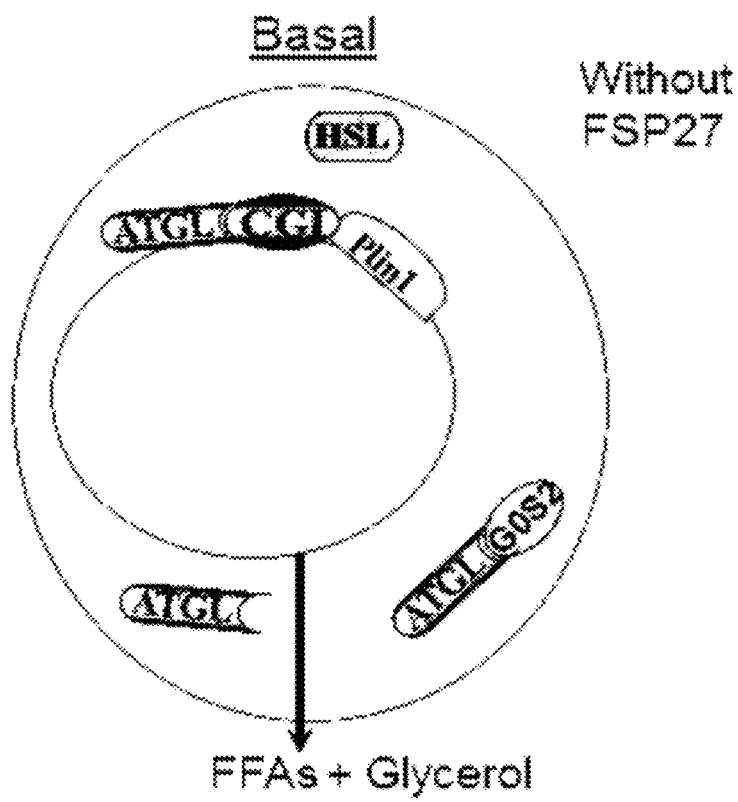

FIG. 1B illustrates that, when FSP27 is absent in basal conditions, ATGL is free to interact with CGI-58, leading to increased lipolysis, as indicated by solid downward arrow.

Figure 1C:
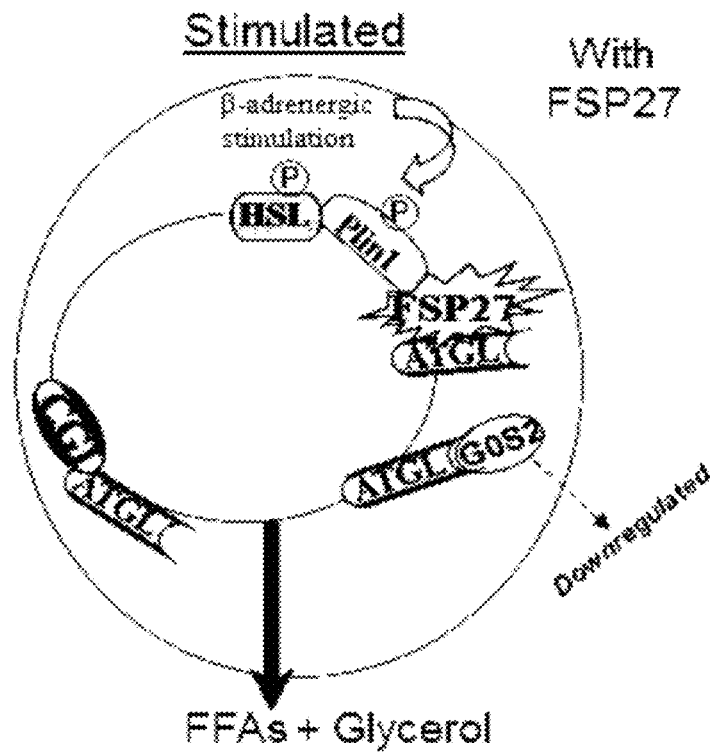

FIG. 1C illustrates that, upon β-adrenergic stimulation in the presence of FSP27, PKA activation results in phosphorylation of PLIN1 and HSL, causing release of CGI-58, which binds to and stimulates ATGL. Unbound ATGL is translocated to lipid droplet and G0S2 is downregulated to increase ATGL-mediated lipolysis as indicated by the bolded downward arrow.

Figure 1D:
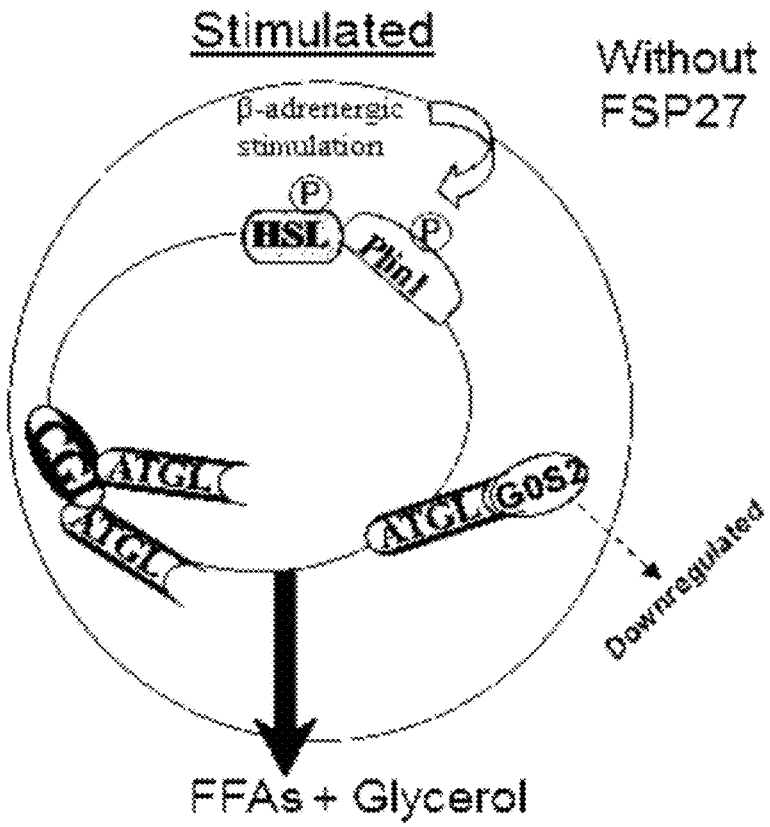

FIG. 1D illustrates that, upon β-adrenergic stimulation in the absence of FSP27, the otherwise FSP27-sequestered-ATGL is now available for CGI-58 binding, resulting in even higher levels of lipolysis, indicated by the more prominent downward arrow.

In addition to inhibiting the access of ATGL to CGI-58, it is now believed that FSP27 affects ATGL-mediated lipolysis in adipocytes by: a) regulating hydrolase activity of ATGL, b) regulating expression and distribution of G0S2, and/or c) that FSP27 depletion causes fragmentation of lipid droplets which increases the surface area of lipid droplets, thus increasing the access of lipases.

The effect of FSP27 on TG hydrolase activity of ATGL is determined by the following protocol: HeLa cells stably expressing or non-expressing FSP27 are transfected with ATGL and CGI-58. The cell homogenates are incubated with $^3$H-labeled triolein as substrate and its hydrolysis is measured. As described in FIGS. 1A-1D, G0/S1 switch gene, G0S2, regulates ATGL-mediated lipolysis via inhibiting its TG hydrolase activity. The distribution of G0S2 is mostly cytosolic but under stimulated conditions a small percentage of it distributes to LDs. Therefore, the effect of expression of FSP27 or its functional domain(s) on the expression and distribution of G0S2 under both basal and/or stimulated conditions in human adipocytes is examined.

FSP27 Depletion Increased Both Basal and Stimulated Lipolysis in Human Adipocytes.

Figure 2A:
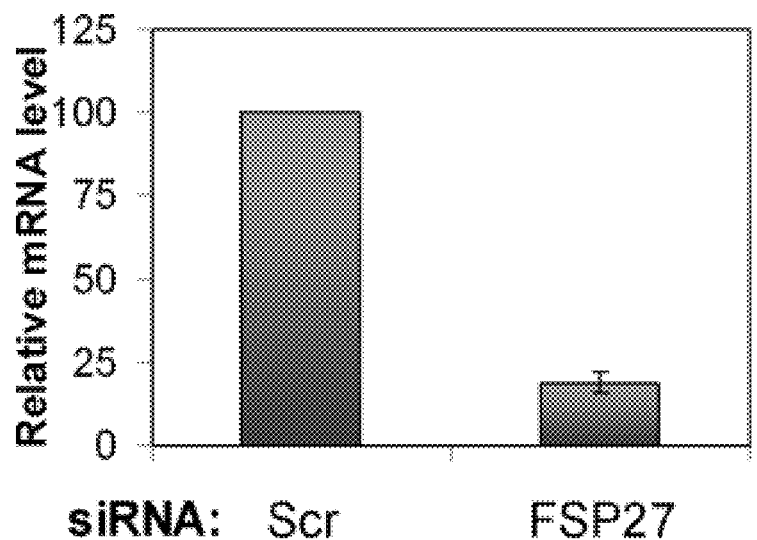
FIGS. 2A-2C: FSP27 depletion increased both basal and stimulated lipolysis in human adipocytes.
Figure 2B:
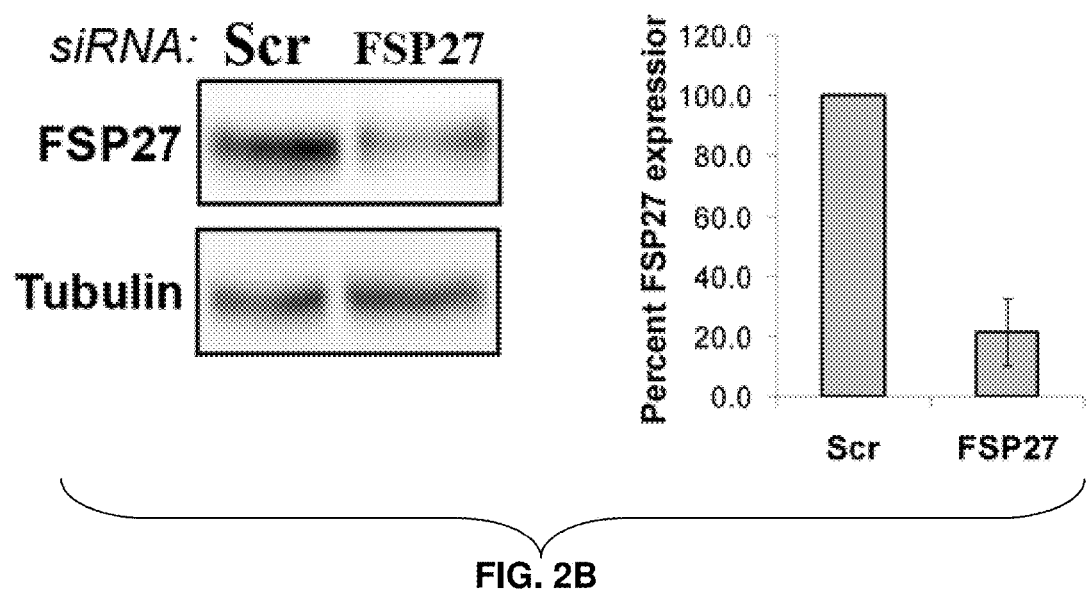
Figure 2C:
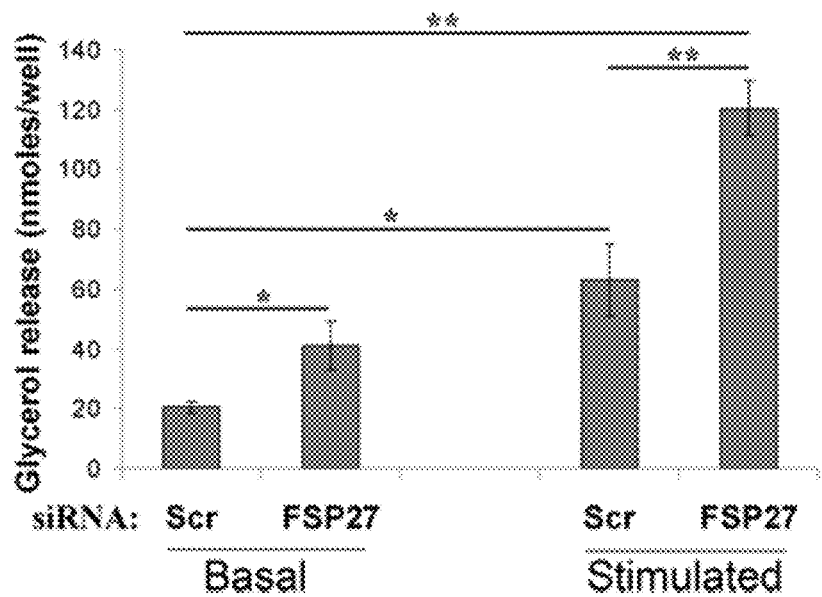

Non-specific scrambled (Scr) siRNA was used as a control in all experiments. FIG. 2A shows the relative mRNA levels in siRNA-transfected human adipocytes. FIG. 2B shows the immunoblot and quantification of protein expression levels of FSP27 and β-tubulin (loading control) of siRNA-transfected human adipocytes. FIG. 2C shows the biochemical quantification of basal and stimulated lipolysis based on measurement of glycerol release after 2 hours. Values are means±standard error; *$p<0.05$ and **$p<0.001$, n=3 (unpaired t-test).

FSP27 Expression Decreased ATGL-Mediated Lipolysis.

Figure 3:
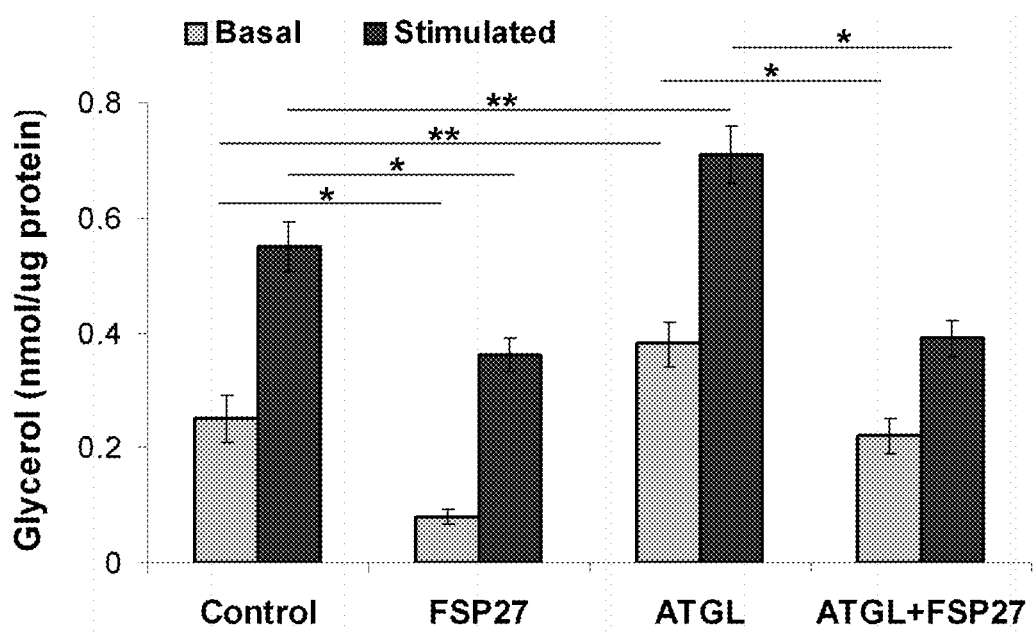
FIG. 3: FSP27 expression decreased ATGL-mediated lipolysis.

FIG. 3 shows glycerol released in cell culture media from human adipocytes expressing EGFP, FSP27-HA and/or ATGL. Control cells were infected with EGFP-containing empty virus. Glycerol released in 2.5 h was measured and normalized to total protein. Values are means±standard error; *$p<0.001$ and **$p<0.05$, n=3 (unpaired t-test).

FSP27 Negatively Regulates ATGL Expression and Lipolysis in Human Adipocytes.

Figure 4A:
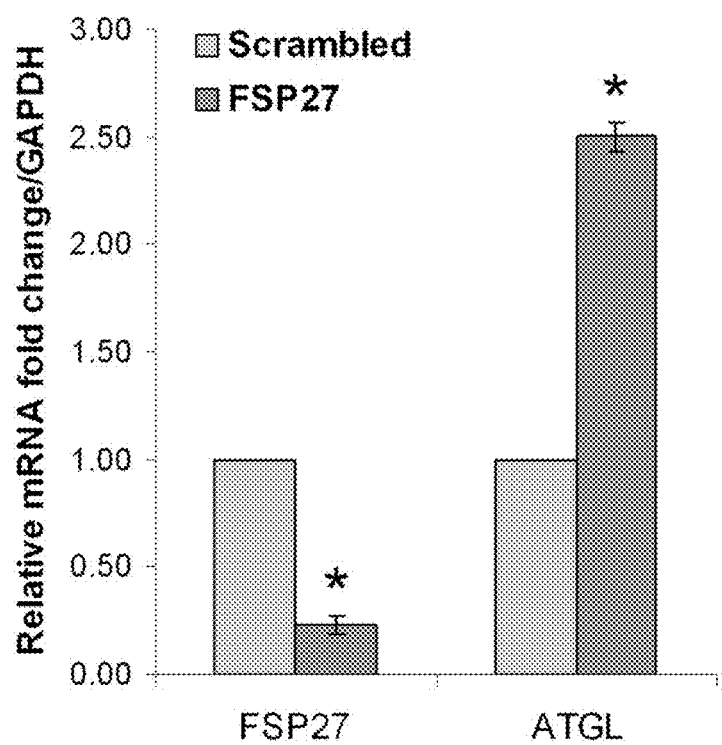
FIGS. 4A-4B: FSP27 negatively regulates ATGL expression and lipolysis in human adipocytes.
Figure 4B:
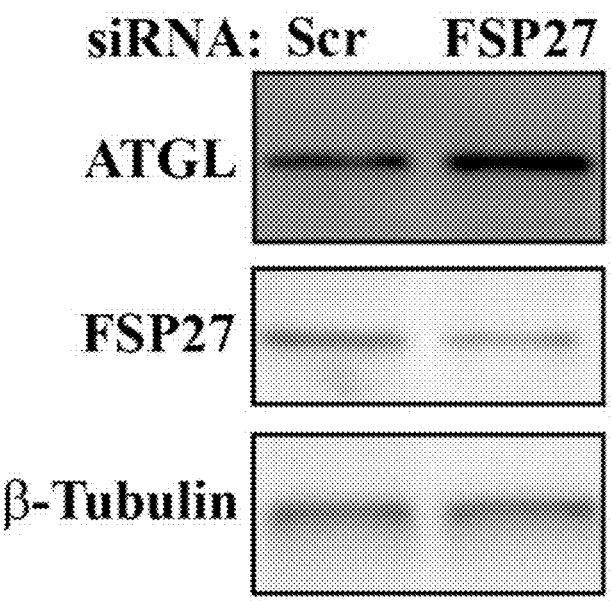

Human adipocytes were cultured and differentiated. FIG. 4A shows where RNA was extracted from control and siRNA-treated adipocytes, and mRNA levels were measured by quantitative PCR and normalized by GAPDH mRNA. The data show an average of three independent experiments. FIG. 4B shows protein lysates from control and siRNA-treated adipocytes were loaded at 15 μg/lane and probed with antibodies against FSP27, ATGL or β-tubulin. Image is representative of at least three independent experiments.

FSP27 Inhibits ATGL Gene Transcription (Promoter/Enhancer) Activity Via Egr1.

FIGS. 5A, 5B, 5D, 5F, and 5G show where HEK293T cells cultured in 12-well dishes were transfected with the full length (−2979/+21), C→T mutated, or truncated ATGL luciferase promoter constructs, cDNA for eGFP; cDNAs for FSP27 and Egr1 as well as scrambled siRNA and Egr1 siRNA as indicated. After 48 h, cells were washed three times in cold PBS and harvested in the reporter lysis buffer. Luciferase activity in cell lysates was assayed and normalized by eGFP fluorescence. Data are presented for triplicate samples as mean±SD; *p<0.05 as estimated by unpaired t-test.

Figure 5A:
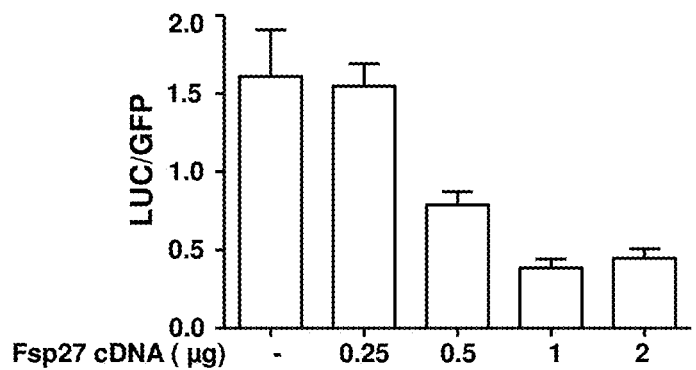
FIGS. 5A-5G: FSP27 inhibits ATGL promoter activity via Egr1.
Figure 5B:
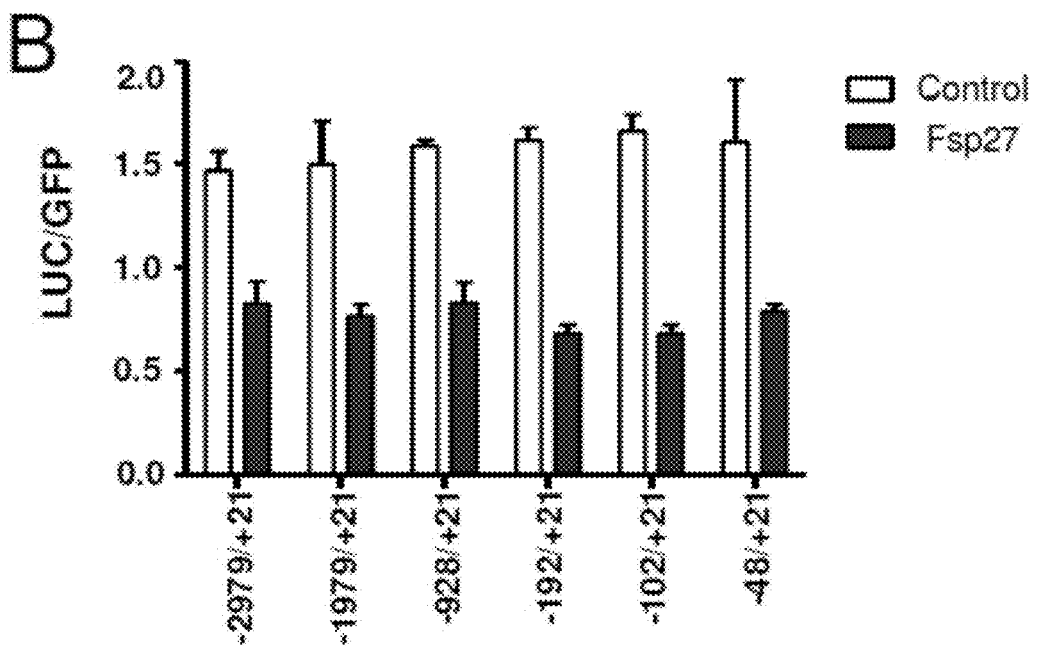
Figure 5C:
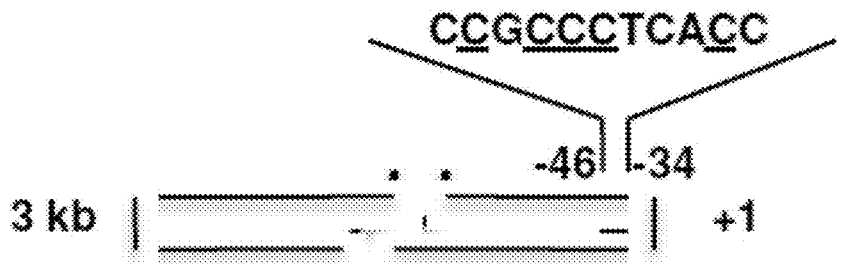
Figure 5D:
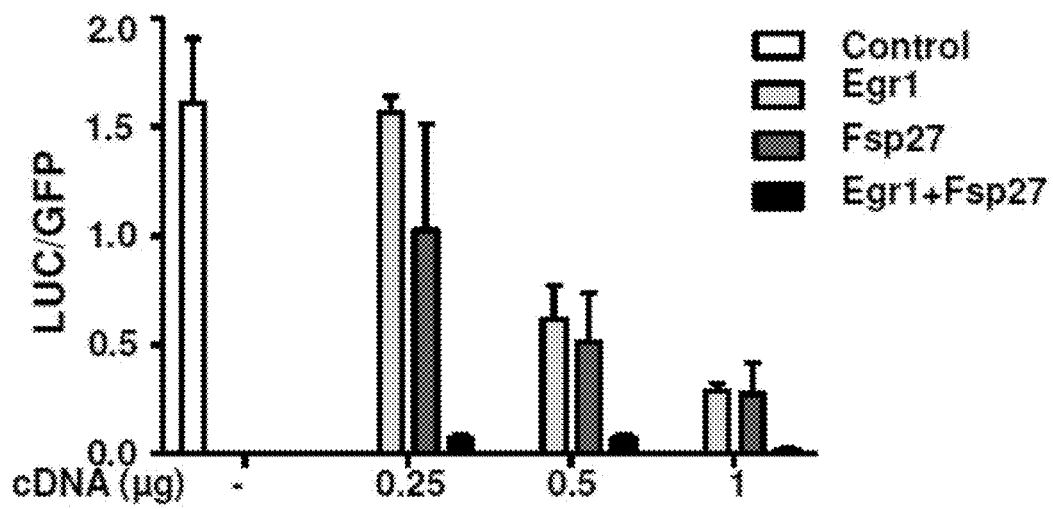

FIG. 5D shows the synergistic effect between Egr1 and FSP27 with p<0.05. Experiments were repeated at least 3 times (FIGS. 5A, 5B, 5D, 5G) and 2 times (FIG. 5F).

FIG. 5C is a schematic representation of the proximal region of ATGL promoter with the consensus Egr1 binding site. Nucleotides that have been chosen for the site-directed mutagenesis are underlined.

Figure 5E:
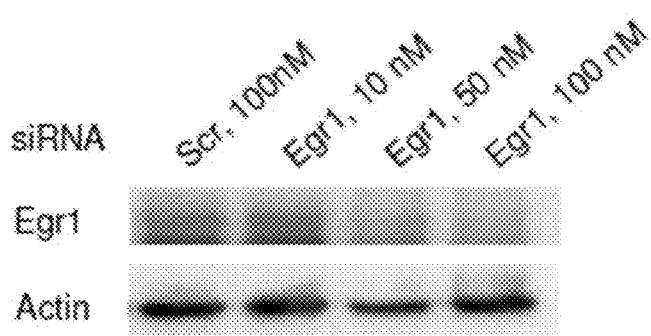
Figure 5F:
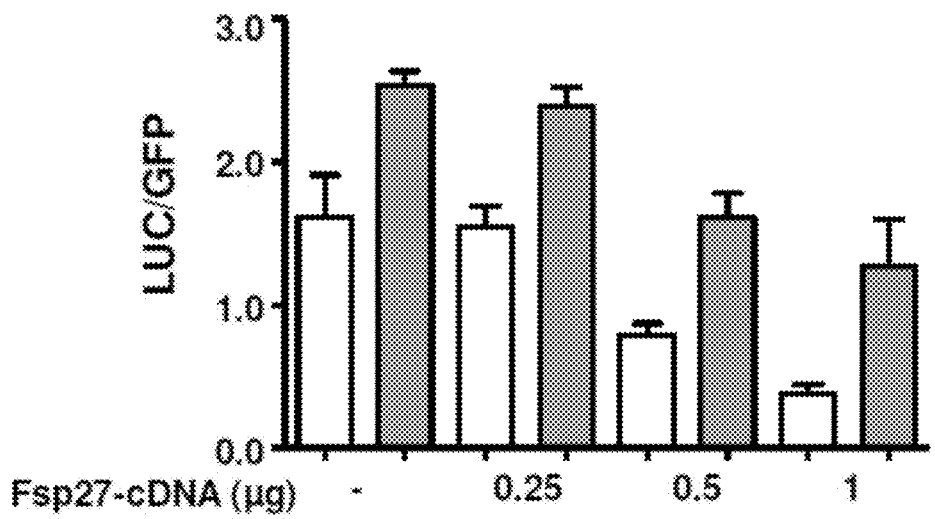
Figure 5G:
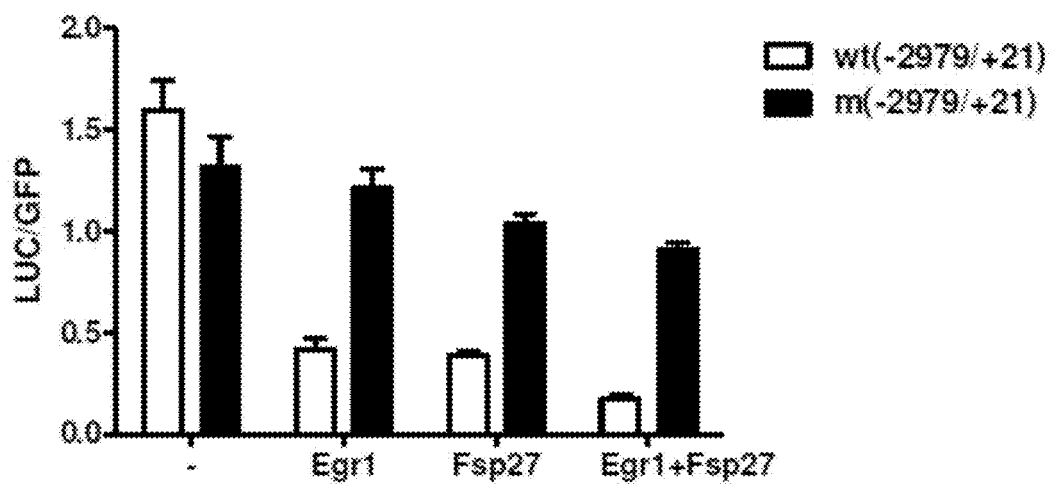

FIG. 5E shows HEK293T cells growing in 35 mm dishes were transfected with scrambled or Egr1 siRNA. Cell lysates were collected 48 h post-transfection, separated by 12.5% PAGE and immunoblotted with Egr1 and actin antibodies. The experiment was repeated at least 2 times.

FSP27 Protected Human Adipocytes Against FFA-Induced Insulin Resistance.

Figure 6A:
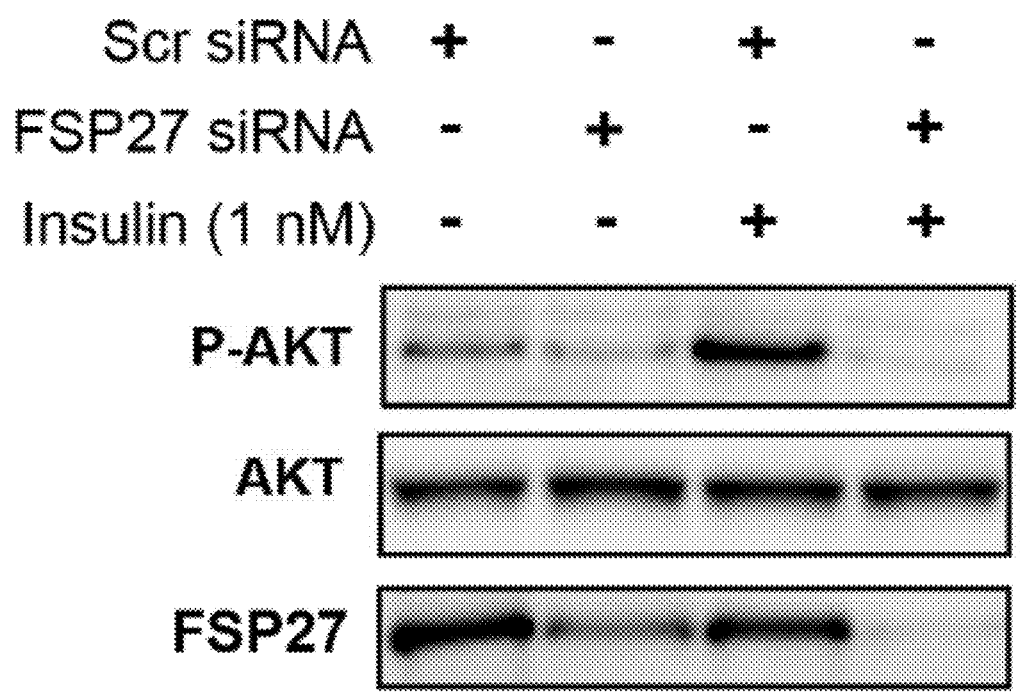
FIGS. 6A-6D: FSP27 protected human adipocytes against FFA-induced insulin resistance.
Figure 6B:
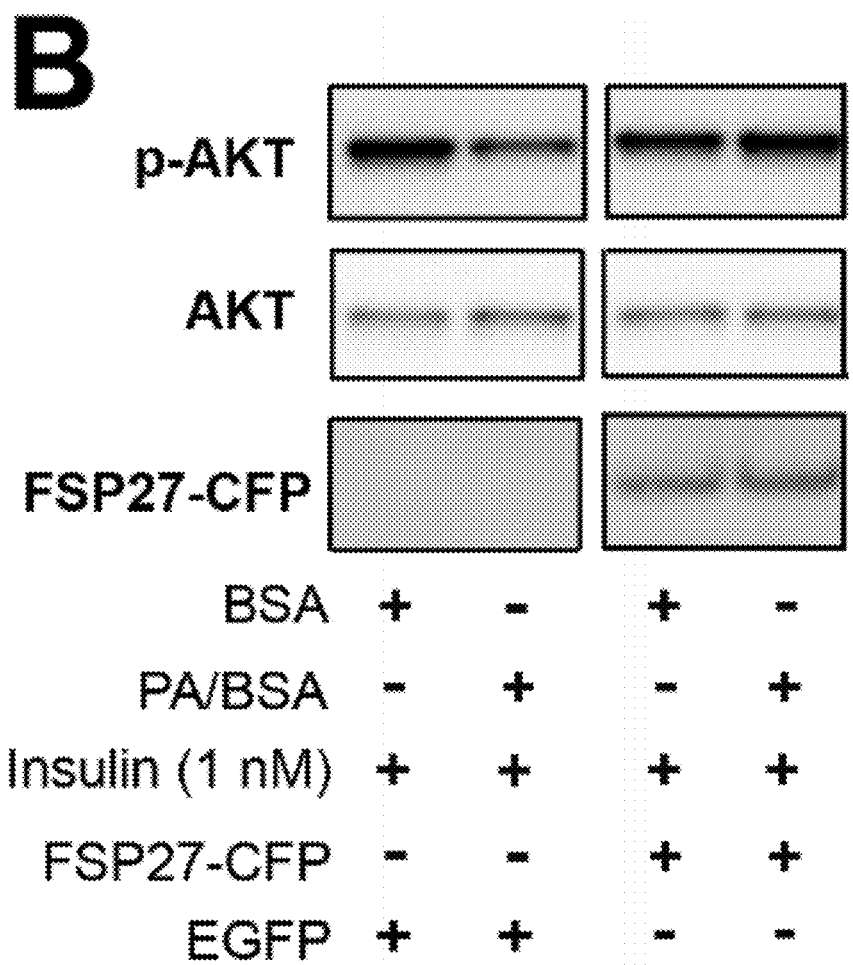
Figure 6C:
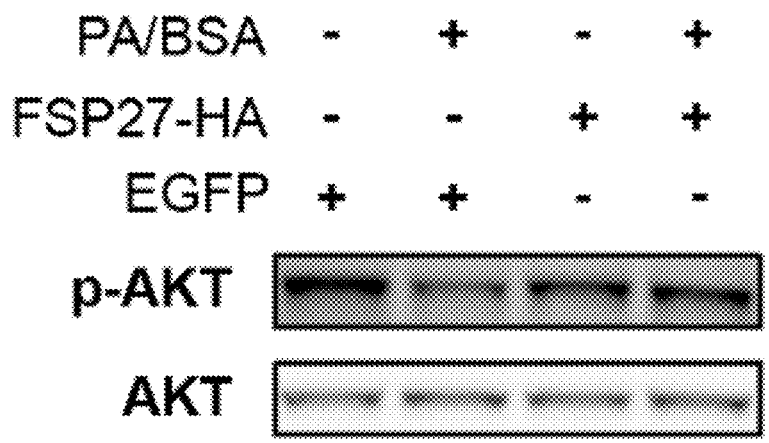
Figure 6D:
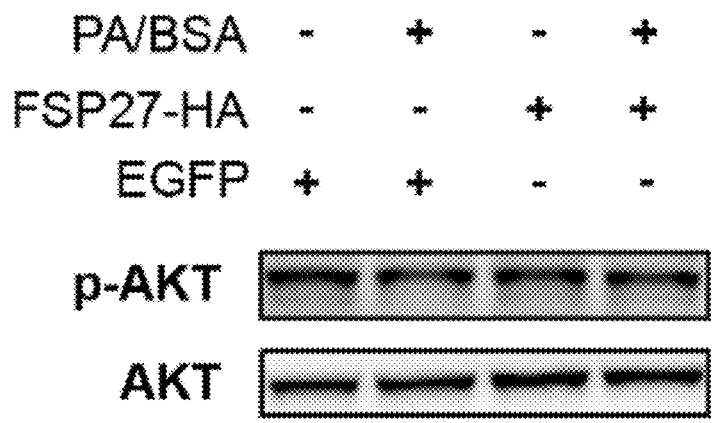

FIG. 6A shows where insulin stimulated AKT phosphorylation in human adipocytes after siRNA-mediated FSP27 knockdown. FIG. 6B shows insulin stimulated AKT phosphorylation in human adipocytes after overnight treatment with 100 μM PA/BSA in the presence or absence of FSP27-CFP or EGFP (Control). FIG. 6C shows FSP27-HA expression protects adipocytes differentiated from WT mouse embryonic fibroblasts (MEFs) against 100 μM PA/BSA-mediated inhibition of insulin stimulated AKT phosphorylation. FIG. 6D shows 100 μM PA/BSA or FSP27-HA expression had no effect on insulin stimulated AKT activation in adipocytes differentiated from ATGL-KO MEFs.

FFAs Impairs Insulin Signaling and Promotes Insulin Resistance in Human Primary Adipocytes.

FSP27 depletion in human adipocytes increased ATGL expression and lipolysis and hence increased FFA levels, and it was determined whether FSP27 depletion affects insulin induced signaling. Indeed, FSP27 knockdown decreased insulin-mediated stimulation of AKT phosphorylation (FIG. 6A). Also, FSP27 overexpression protected human adipocytes against FFA-induced insulin resistance (FIG. 6B).

Furthermore, adipocytes derived from ATGL-KO MEFs but not WT were resistant to FFA-induced insulin resistance (FIG. 6C and FIG. 6D).

Figure 7:
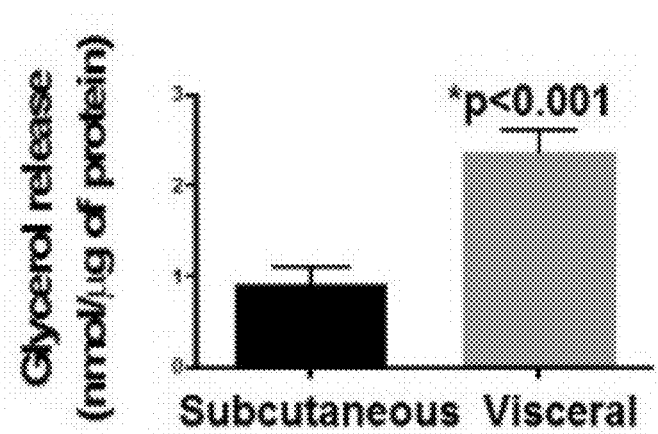
FIG. 7: Basal lipolysis was significantly higher in visceral depots compared to subcutaneous. Glycerol release was measured in 12 subcutaneous, 15 omentum adipose depots and normalized to total μg of protein. Data are presented as ±SEM.

FIG. 7 shows that basal lipolysis was significantly higher in visceral depots compared to subcutaneous. Glycerol release was measured in 12 subcutaneous, 15 omentum adipose depots and normalized to total μg of protein. Data are presented as ±SEM.

Increased Lipolysis in Visceral Adipose Negatively Correlates with FSP27 Expression.

Figure 8A:
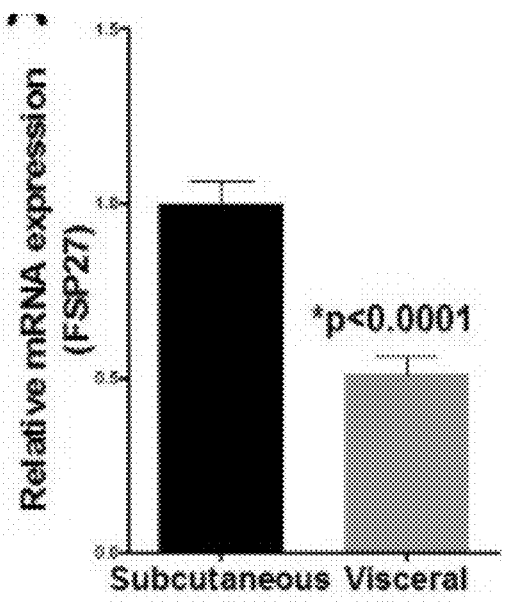
FIGS. 8A-8B: Increased lipolysis in visceral adipose negatively correlates with FSP27 expression.
Figure 8B:
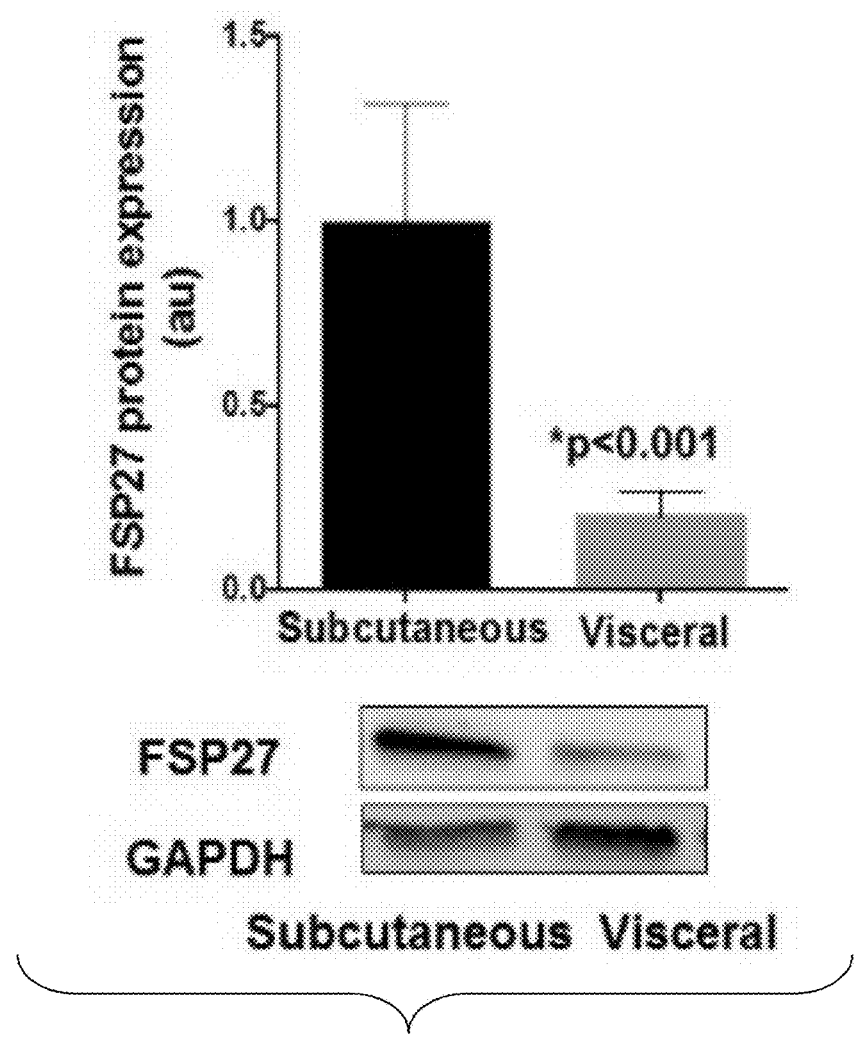

FIG. 8A shows that basal FSP27 was significantly higher in subcutaneous depot. FSP27 mRNA was measured in 27 paired samples from subcutaneous and omentum depots. Data are presented as ±SEM. FIG. 8B shows basal FSP27 protein was measured in 13 paired subcutaneous, omentum depots. Data are presented as ±SEM.

Effect of FSP27 Depletion on Insulin Signaling in Adipocytes.

Akt activation is regulated by PIP3, and PIP3 levels are tightly regulated by phosphatidylinositol (PI)-3K and phosphatases, such as PTEN, which antagonizes PI3K/Akt signaling by dephosphorylating PIP3. The phosphorylation of PTEN is measured at $Ser^{380}/Thr^{382}/Thr^{383}$. Also, the phosphorylation of IRS-1 and AS160 is measured and compared with the expression of FSP27.

Figure 9A:
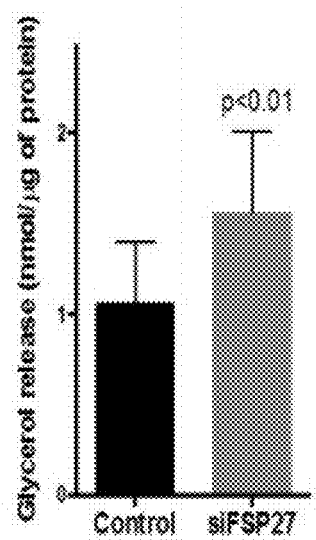
FIGS. 9A-9B: siRNA-mediated FSP27 knockdown increases lipolysis and impairs insulin signaling.
Figure 9B:
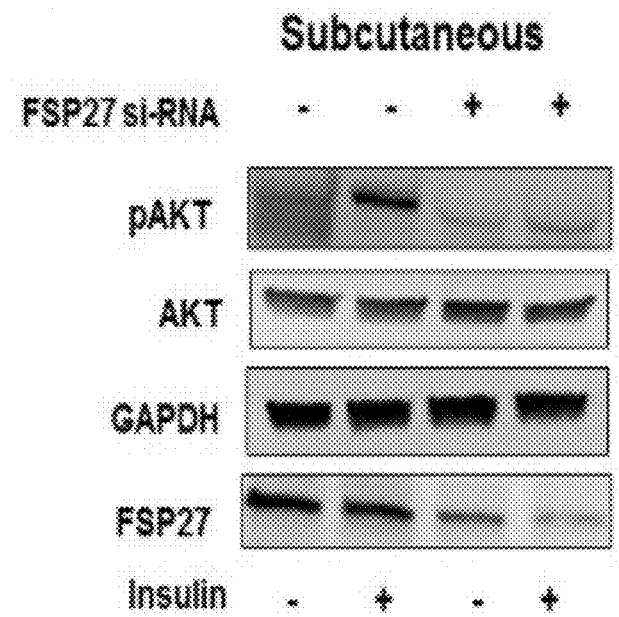

FSP27 expression was lower in visceral adipose depot of a cohort of obese human subjects, as shown in FIGS. 8A-8B. The phosphorylation of IRS-1 and AS160 is measured in both visceral and subcutaneous adipose tissue of obese human subjects and compared with FSP27 expression FIGS. 9A-9B show that siRNA-mediated FSP27 knockdown increases lipolysis and impairs insulin signaling. FIG. 9A shows knockdown of FSP27 in subcutaneous adipose tissue increased rate of glycerol release in the media. Data are presented as ±SEM (n=7). FIG. 9B shows siRNA-mediated FSP27 depletion decreased Akt phosphorylation.

The involvement of activated JNK and p38 stress pathways in FSP27-depleted inhibition of Akt in adipocytes and muscle and liver cells. FSP27 depletion increases lipolysis and FFA release in human adipocytes. Since FFAs increase ceramide content, which has been shown to activate MLK3, the upstream kinase of JNK and p38 pathways, the activation of these pathways. JNK and p38 are activated by phosphorylation at $Thr^{183}/Tyr^{185}$ and $Thr^{180}/Tyr^{182}$, respectively, FSP27 depletion increases lipolysis and FFA release in human adipocytes. Since FFAs increase ceramide which activates MLK3, an upstream kinase for JNK and p38. Phosphorylation of JNK and p38 by MLK3 at $Thr^{183}/Tyr^{185}$ and $Thr^{180}/Tyr^{182}$, respectively, causes downregulation of insulin receptor signaling in adipose, muscle and liver cells to promote insulin resistance.)

Recombinant FSP27 Improves Insulin Signaling in Visceral Adipose.

Figure 10A:
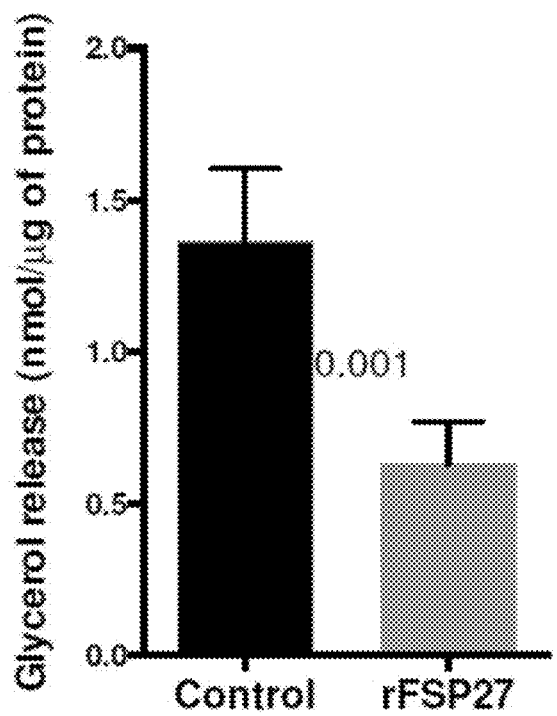
FIGS. 10A-10B: Recombinant FSP27 improves insulin signaling in visceral adipose.
Figure 10B:
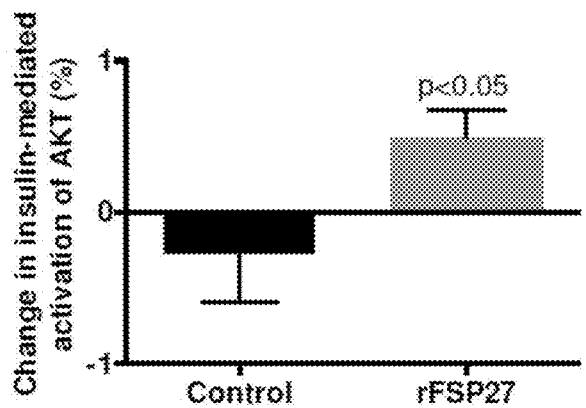

FIG. 10A shows the treatment of visceral depot with recombinant FSP27 decreased basal lipolysis. FIG. 10B shows the quantification of insulin-stimulated AKT phosphorylation. Data are presented as ±SEM. *p<0.05.

FSP27 (120-220) Protects Against FFA-Induced Insulin Resistance in Human Adipocytes.

Figure 11:
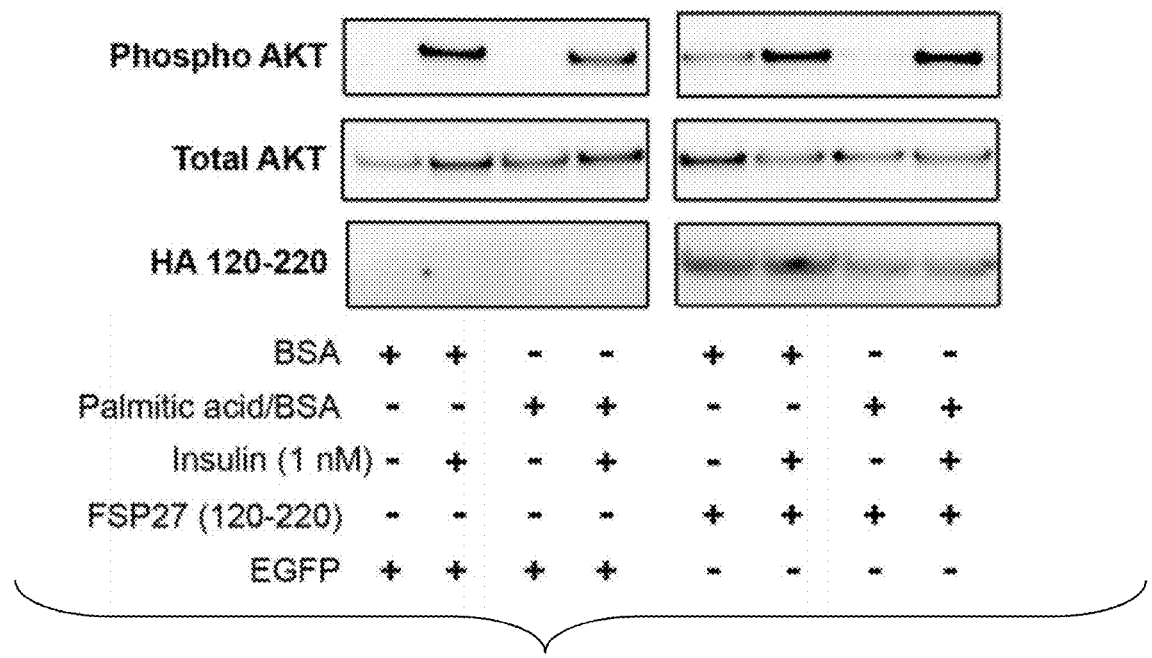
FIG. 11: FSP27 (120-220) protected against FFA-induced insulin resistance in human primary adipocytes.

Insulin stimulated AKT phosphorylation in human adipocytes. The core FSP27 domain that is associated with TG accumulation, aa 120-220, was expressed using lentivirus, with EGFP as a control. The cells were treated overnight with 100 μM PA/BSA. The blots in FIG. 11 show AKT phosphorylation in basal and insulin stimulated conditions. FSP27 (120-220) protected human adipocytes from inhibition of AKT phosphorylation by exogenous PA.

FIG. 12 shows the schematic representation of FSP27 and its functional domains: CIDE-N terminal domain and CIDE-C terminal domain. The N-terminus of FSP27 is from amino acids 1-120 and the C-terminus is from amino acids 121-239. FSP27-mediated enlargement of lipid droplets (LDs) consists of two independent steps, clustering followed by fusion of LDs. Amino acids 172-210 are necessary and sufficient for FSP27-mediated clustering of LDs. The clustering of LDs has no effect on their size and cellular TG levels. The LD clustering is followed by their enlargement. Amino acids 120-210 are sufficient for clustering and enlargement of LDs.

Figure 13:
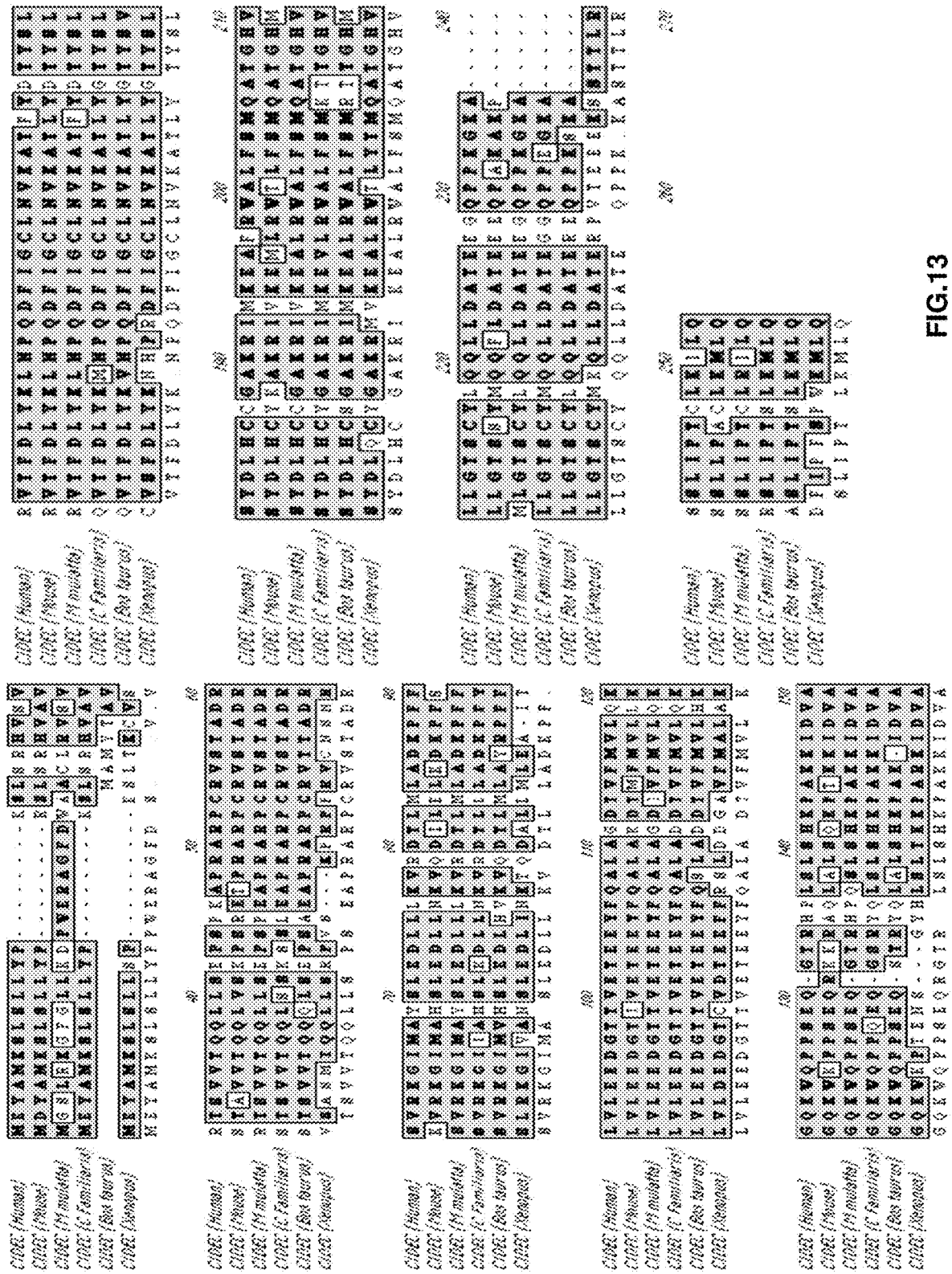
FIG. 13: FSP27 sequence is conserved in vertebrates; for example, >90% conserved sequence in FSP27 in humans, mouse, monkey, dog, cow and frog.

FIG. 13 shows that the FSP27 sequence is conserved in vertebrates; for example, >90% conserved sequence in FSP27 in humans, mouse, monkey, dog, cow and frog.

Generation of Adipose Specific Human FSP27-Overexpressing Transgenic Mice.

FSP27-mediated suppression of lipolysis in adipose tissue can protect from insulin resistance and Type 2 diabetes.

FSP27 was cloned in ROSA26-CMV-loxSTOPlox vector and mice generated conditionally over-express FSP27. These mice are crossed with Adipoq-cre mice to specifically over-express FSP27 in adipose tissue (AT), (AT-FSP27tg). Based upon the data shown in FIGS. 6A-6D, a 2-3 fold increase in FSP27 expression in WAT it is now believed to be sufficient to provide a protective effect of FSP27 against high Fat Diet (HFD)-induced insulin resistance.

In order to determine whether overexpressing FSP27 also alters other proteins associated with lipid droplet protection and lipolysis, PLIN1, ATGL and HSL protein and/or phosphorylation are analyzed under basal and stimulated states; then followed with identifying any alterations in adipocyte lipolysis. Fat deposition and lipid metabolites in muscle and liver are measured in the experimental animals. To estimate intracellular pools of FSP27, lipid droplet pools of FSP27 are isolated and quantified. The amount of FSP27 is expressed relative to the number and/or surface area of adipocytes.

Glucose Homeostasis and Metabolic Phenotyping:

The littermates are subjected to physiological characterization at 6, 12 and 26 weeks. Body weights and body composition are measured by Magnetic Resonance Imaging. Under both fed and fasted conditions, level of circulating, glucose, insulin, FFA, glycerol, GH, IGF-1 and adipokines (leptin, resistin, and adiponectin) are determined with commercially available ELISA or enzymatic kits. Intraperitoneal glucose tolerance testing (GTT) (2 g/kg body weight), and intraperitoneal insulin tolerance test (ITT) (0.75-1.25 U/kg body weight) are assessed. Separate cohorts of mice are placed on either a low (10%) or high (60%) fat diet (HFD) (D12450B and D12492, Research Diets) for 12 wks and studied in a similar manner. Changes in metabolic rate and energy expenditure are measured by the Comprehensive Lab Animal Monitoring System (CLAMS, Columbus Instrument). Mice are acclimated for 24 h then monitored for a 48 h fed period followed by a 24 h fasted period. Activity (determined by infrared beam breaks), food intake, energy expenditure (normalized to lean body mass) and heat production are also measured. Respiratory exchange ratio (RER) (VCO2/VO2) is calculated from the gas exchange data for light and dark phases. After completion of the physiological assessment, mice are sacrificed. Blood, skeletal muscles (quadriceps, EDL, and tibialis anterior), liver, heart, kidney, subcutaneous (SC), perigonaldal (PG), and brown fat depots, brain, and pancreas and/or isolated islets are collected and weighed. Tissues are prepared for histology and mRNA and protein is extracted for further analysis.

Insulin Signaling, Glucose Uptake, and Lipolysis:

Results from the hyperinsulinemic-euglycemic clamp and ITT are confirmed by assessing insulin signaling in insulin sensitive tissues, including the adipose tissue (AT), muscle, and liver. Fifteen minutes after intravenous injection of insulin, tissues are isolated and insulin signaling intermediates (e.g. IR, IRS1, Akt, PI3K, and mTORC1 and, where relevant, their phosphorylated counterparts) are assayed by western blot analysis. For measurements of glucose uptake and lipolysis from primary adipocytes, fat pads are enzymatically digested. Lipolytic rate is quantified by glycerol and FA release, and glucose uptake is determined by uptake of [$^3$H] 2-Deoxy-D-glucose. Since adipocyte size is believed to vary in these mouse models, we will quantify lipolysis "per adipocyte" and "per unit adipocyte surface area" are quantified.

Histology of Adipose Tissue, Ectopic Lipid and Cytokine Quantitation:

AT histology is conducted to examine the adipocyte morphology and macrophage infiltration. Adipocyte size and macrophage infiltration are quantified. Ectopic fat deposition in muscle and liver is visualized by histology and triacylglycerol, diacylglycerol, and ceramides are quantified. The circulating levels and mRNA expression of pro-inflammatory cytokines (IL1β, TNFα, IL6) are determined, as FFAs have been shown to modulate macrophage activation and the expression of pro-inflammatory cytokines. Furthermore, TNFα has been shown to increase lipolysis in a FSP27 dependent manner.

Protected Insulin and Glucose Response in High-Fat Fed Adipose Tissue-Specific Human-FSP27 Transgenic Mice (AT-hFSP27tg).

Figure 14A:
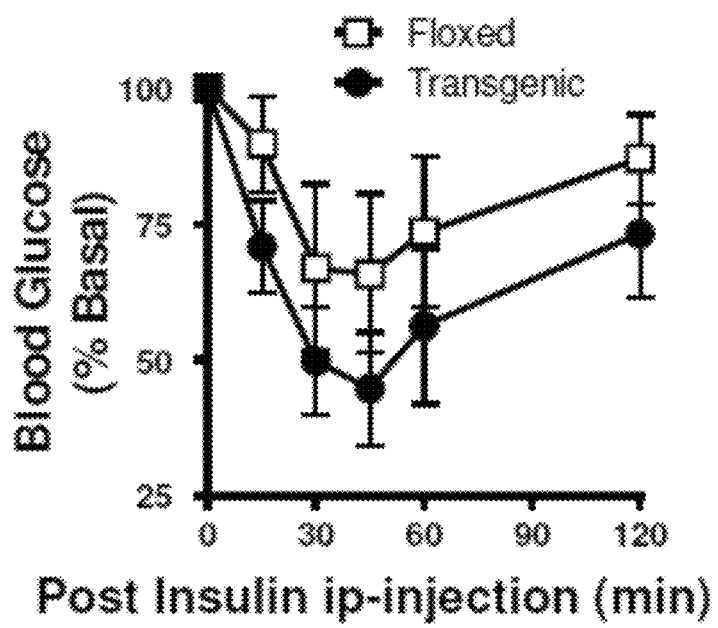
FIG. 14A: Insulin tolerance test (ITT) in AT-hFSP27tg mice.
Figure 14A:
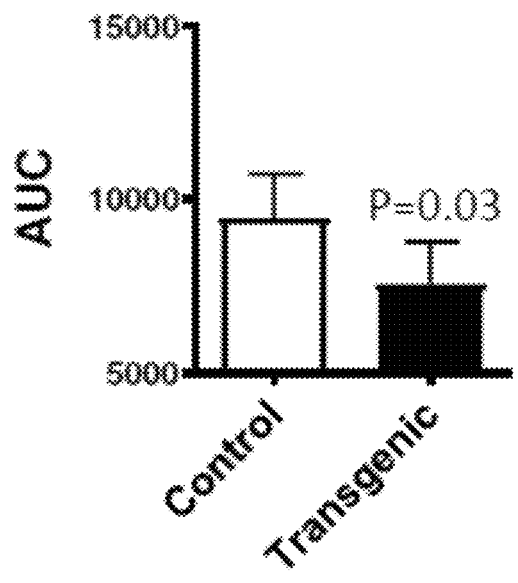
Figure 14B:
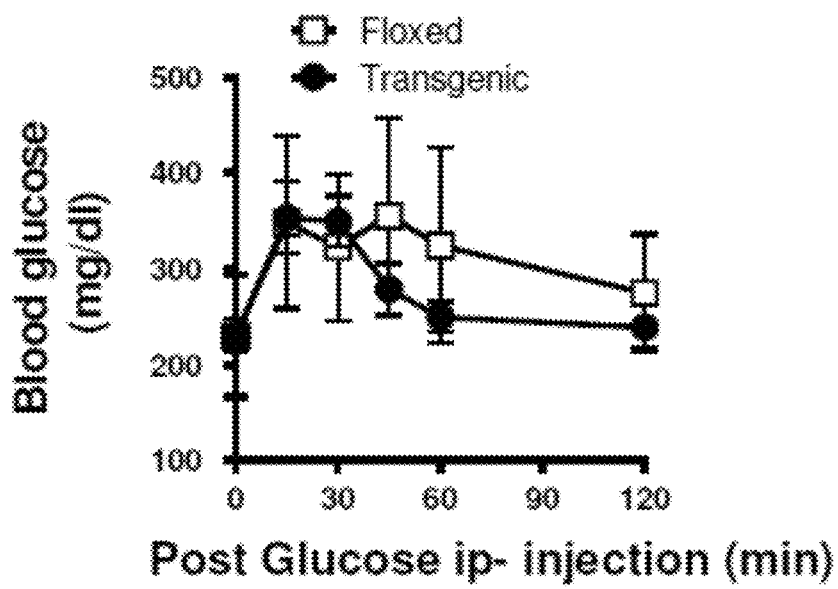
FIG. 14B: Glucose tolerance test (GTT) in AT-hFSP27tg mice.
Figure 14B:
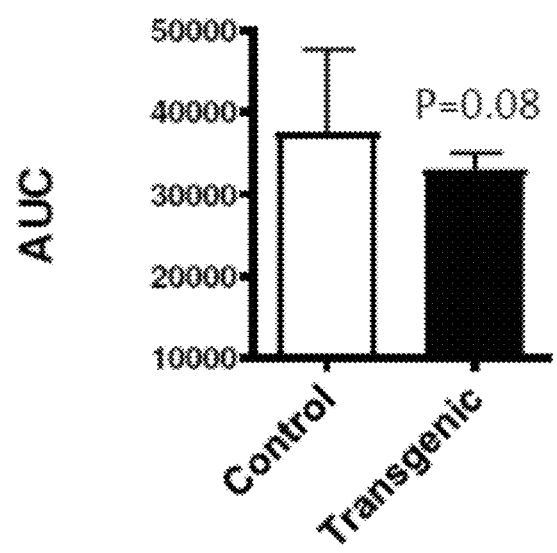

FIG. 14A shows insulin tolerance test (ITT), while FIG. 14B shows glucose tolerance test (GTT) in AT-hFSP27tg mice. Males (5-month-old, n=3/group) were fed a 60% HF for 3 months. Data: mean±SEM. Plots at the bottom of the curves show area under the curves. These data show that overexpressing FSP27 in adipocytes prevents diet-induced insulin resistance.

FSP27 Knockout (FSP27$^{-/-}$) are Glucose and Insulin Intolerant.

Figure 15A:
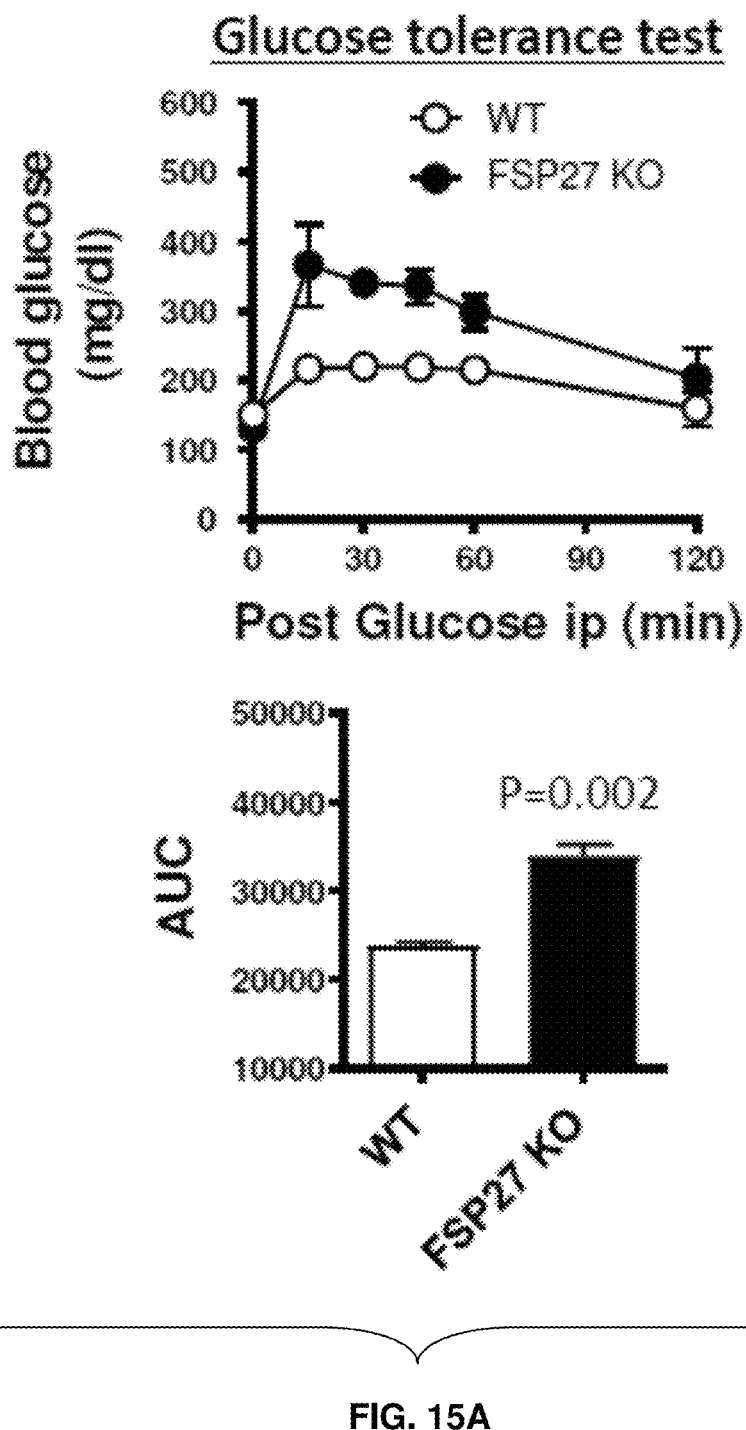
FIG. 15A: Glucose tolerance test (GTT) in FSP27$^{-/-}$ mice.
Figure 15B:
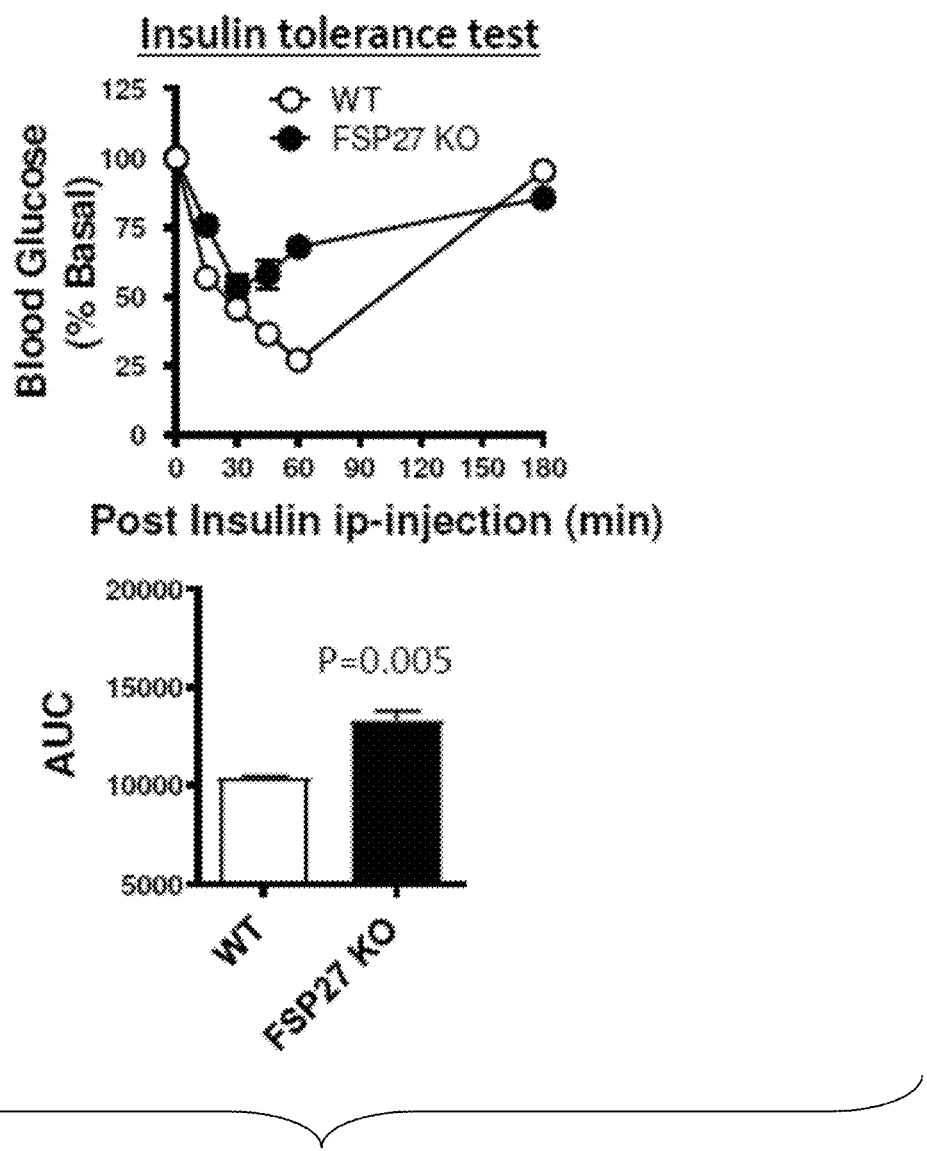
FIG. 15B: Insulin tolerance test (ITT) in FSP27$^{-/-}$ mice.

FIG. 15A shows glucose tolerance test (GTT), while FIG. 15B shows insulin tolerance test (ITT) in FSP27$^{-/-}$ mice. Males (4 month-old; n=3/group) Data: mean±SEM; p<0.05 in Fsp27$^{-/-}$ vs Wild type (WT) mice. Plots at the bottom of the curves show area under the curves.

Plasma Insulin and NEFA in FSP27$^{-/-}$ Mice on a Regular Diet (RD)

Figure 16A:
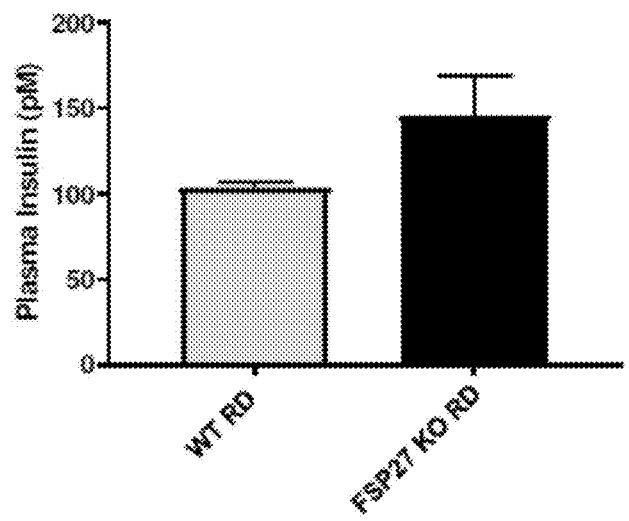
FIG. 16A: Fasting blood insulin in FSP27 knockout mice.
Figure 16B:
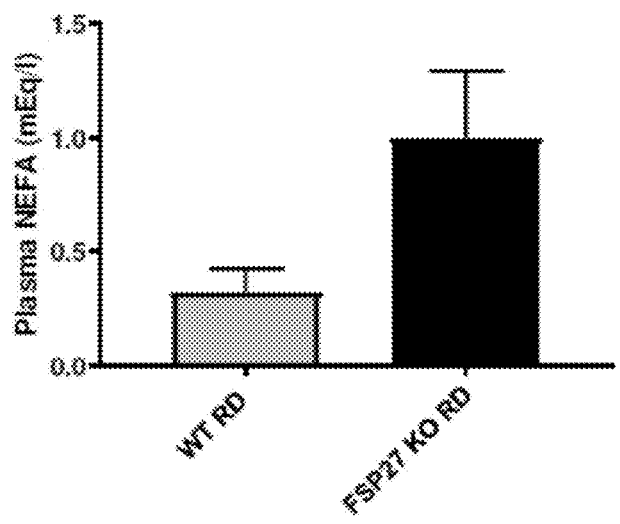
FIG. 16B: Non-esterified fatty acid (NEFA) (Free fatty acids) in FSP27 knockout mice.

Fasting blood insulin and non-esterified fatty acid (Free fatty acids) levels were higher in FSP27 knockout mice, as shown in FIG. 16A and FIG. 16B.

Pharmaceutical Compositions

A pharmaceutical composition as described herein may be formulated with any pharmaceutically acceptable excipients, diluents, or carriers. A composition disclosed herein may comprise different types of carriers depending on whether it is to be administered in solid, liquid, or aerosol form, and whether it needs to be sterile for such routes of administration as injection. Compositions disclosed herein can be administered in a suitable manner, including, but not limited to topically (i.e., transdermal), subcutaneously, by localized perfusion bathing target cells directly, via a lavage, in creams, in lipid compositions (e.g., liposomes), formulated as elixirs or solutions for convenient topical administration, formulated as sustained release dosage forms, or by other method or any combination of the forgoing as would be known to one of ordinary skill in the art (see, for example, Remington's Pharmaceutical Sciences, 2003, incorporated herein by reference).

The compositions provided herein are useful for treating animals, such as humans. A method of treating a human patient according to the present disclosure includes the administration of a composition, as described herein.

The phrases "pharmaceutical" or "pharmacologically acceptable" refer to molecular entities and compositions that produce no adverse, allergic, or other untoward reaction when administered to an animal, such as, for example, a human. A carrier or diluent may be a solid, semi-solid, or liquid material which serves as a vehicle, excipient, or medium for the active therapeutic substance. Some examples of the diluents or carriers which may be employed in the pharmaceutical compositions of the present disclosure are lactose, dextrose, sucrose, sorbitol, mannitol, propylene glycol, liquid paraffin, white soft paraffin, kaolin, fumed silicon dioxide, microcrystalline cellulose, calcium silicate, silica, polyvinylpyrrolidone, cetostearyl alcohol, starch, modified starches, gum acacia, calcium phosphate, cocoa butter, ethoxylated esters, oil of theobroma, arachis oil, alginates, tragacanth, gelatin, syrup, methyl cellulose, polyoxyethylene sorbitan monolaurate, ethyl lactate, methyl and propyl hydroxybenzoate, sorbitan trioleate, sorbitan sesquioleate and oleyl alcohol, and propellants such as trichloromonofluormethane, dichlorodifluoromethane, and dichlorotetrafluoroethane.

Solutions of the compositions disclosed herein as free bases or pharmacologically acceptable salts may be prepared in water suitably mixed with a surfactant, such as hydroxypropylcellulose. Dispersions may also be prepared in glycerol, liquid polyethylene glycols, and mixtures thereof, and in oils. Under ordinary conditions of storage and use, these preparations contain a preservative to prevent the growth of microorganisms. The pharmaceutical forms suitable for use include sterile aqueous solutions or dispersions and sterile powders for the extemporaneous preparation of sterile solutions or dispersions. In certain cases the form should be sterile and should be fluid to the extent that easy injectability exists. It should be stable under the conditions of manufacture and storage and may optionally be preserved against the contaminating action of microorganisms, such as bacteria and fungi. The carrier can be a solvent or dispersion medium containing, for example, water, ethanol, a polyol (i.e., glycerol, propylene glycol, and liquid polyethylene glycol, and the like), suitable mixtures thereof, and/or vegetable oils. The prevention of the action of microorganisms can be brought about by various antibacterial and antifungal agents, for example, parabens, chlorobutanol, phenol, sorbic acid, thimerosal, and the like. In many cases, it may be preferable to include isotonic agents, such as, but not limited to, sugars or sodium chloride.

Pharmaceutical compositions for topical administration may include the compositions formulated for a medicated application such as an ointment, paste, cream, or powder. Ointments include all oleaginous, adsorption, emulsion, and water-soluble based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and laurocapram. Possible bases for compositions for topical application include polyethylene glycol, lanolin, cold cream, and petrolatum as well as any other suitable absorption, emulsion, or water-soluble ointment base. Topical preparations may also include emulsifiers, gelling agents, and antimicrobial preservatives as necessary to preserve the composition and provide for a homogenous mixture. Transdermal administration of the compositions may also comprise the use of a "patch." For example, the patch may supply one or more compositions at a predetermined rate and in a continuous manner over a fixed period of time.

It is further envisioned the compositions disclosed herein may be delivered via an aerosol. The term aerosol refers to a colloidal system of finely divided solid or liquid particles dispersed in a liquefied or pressurized gas propellant. The typical aerosol comprises a suspension of active ingredients in liquid propellant or a mixture of liquid propellant and a suitable solvent. Suitable propellants include hydrocarbons and hydrocarbon ethers. Suitable containers can vary according to the pressure requirements of the propellant. Administration of the aerosol can vary according to subject's age, weight, and the severity and response of the symptoms.

Dosage

The actual dosage amount of a composition disclosed herein administered to an animal or human patient can be determined by physical and physiological factors such as body weight, severity of condition, the type of disease being treated, previous or concurrent therapeutic interventions, idiopathy of the patient, and the route of administration. Depending upon the dosage and the route of administration, the number of administrations of a preferred dosage and/or an effective amount may vary according to the response of the subject. The compounds of the present disclosure are generally effective over a wide dosage range. The practitioner responsible for administration can, in any event, determine the concentration of active ingredient(s) in a composition and appropriate dose(s) for the individual subject.

Naturally, the amount of active compound(s) in each therapeutically useful composition may be prepared in such a way that a suitable dosage can be obtained in any given unit dose of the compound. Factors such as solubility, bioavailability, biological half-life, route of administration, product shelf life, as well as other pharmacological considerations can be contemplated by those preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above. The dosages can depend on many factors, and can in any event be determined by a suitable practitioner. Therefore, the dosages described herein are not intended to be limiting In some embodiments, the compositions further include an additional active ingredient. The preparation of a pharmaceutical composition that contains at least one compound or additional active ingredient can be known to those of skill in the art in light of the present disclosure, as exemplified by Remington's Pharmaceutical Sciences, 2003, incorporated herein by reference. Moreover, for animal (e.g., human) administration, it can be understood that preparations should meet sterility, pyrogenicity, and general safety and purity standards as required by the FDA Office of Biological Standards.

Packaging of the Composition

After formulation, the composition is packaged in a manner suitable for delivery and use by an end user. In one embodiment, the composition is placed into an appropriate dispenser and shipped to the end user. Examples of final container may include a pump bottle, squeeze bottle, jar, tube, capsule or vial.

The compositions and methods described herein can be embodied as parts of a kit or kits. A non-limiting example of such a kit comprises the ingredients for preparing a composition, where the containers may or may not be present in a combined configuration. In certain embodiments, the kits further comprise a means for administering the composition, such as a topical applicator, or a syringe. The kits may further include instructions for using the components of the kit to practice the subject methods. The instructions for practicing the subject methods are generally recorded on a suitable recording medium. For example, the instructions may be present in the kits as a package insert or in the labeling of the container of the kit or components thereof. In other embodiments, the instructions are present as an electronic storage data file present on a suitable computer readable storage medium, such as a flash drive, CD-ROM, or diskette. In other embodiments, the actual instructions are not present in the kit, but means for obtaining the instructions from a remote source, such as via the internet, are provided. An example of this embodiment is a kit that includes a web address where the instructions can be viewed and/or from which the instructions can be downloaded. As with the instructions, this means for obtaining the instructions is recorded on a suitable substrate.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof.

Therefore, it is intended that the invention not be limited to the particular embodiment disclosed herein contemplated for carrying out this invention, but that the invention will include all embodiments falling within the scope of the claims.

What is claimed is:

1. A pharmaceutical composition comprising a nucleic acid encoding a Fat Specific Protein 27 (FSP27) sequence as an active ingredient wherein said composition exhibits a decrease in lipolysis in adipocytes in a patient; wherein the nucleic acid encoding the FSP27 sequence consists of amino acid residues at positions 120-220 of SEQ ID NO: 2, together with one or more non-naturally occurring excipients, carriers and/or diluents.

2. The pharmaceutical composition of claim 1, wherein the nucleic acid is present in an amount sufficient to promote a decrease in adipocytes in the patient suffering from dyslipidemia.

* * * * *

```
                          SEQUENCE LISTING

Sequence total quantity: 7
SEQ ID NO: 1            moltype = DNA  length = 11
FEATURE                 Location/Qualifiers
source                  1..11
                        mol_type = unassigned DNA
                        organism = unidentified
                        note = Description of Unknown: Egr1 binding site
SEQUENCE: 1
ccgccctcac c                                                              11

SEQ ID NO: 2            moltype = AA   length = 238
FEATURE                 Location/Qualifiers
source                  1..238
                        mol_type = protein
                        organism = Homo sapiens
SEQUENCE: 2
MEYAMKSLSL LYPKSLSRHV SVRTSVVTQQ LLSEPSPKAP RARPCRVSTA DRSVRKGIMA   60
YSLEDLLLKV RDTLMLADKP FFLVLEEDGT TVETEEYFQA LAGDTVFMVL QKGQKWQPPS  120
EQGTRHPLSL SHKPAKKIDV ARVTFDLYKL NPQDFIGCLN VKATFYDTYS LSYDLHCCGA  180
KRIMKEAFRW ALFSMQATGH VLLGTSCYLQ QLLDATEEGQ PPKGKASSLI PTCLKILQ    238

SEQ ID NO: 3            moltype = AA   length = 239
FEATURE                 Location/Qualifiers
source                  1..239
                        mol_type = protein
                        organism = Mus sp.
SEQUENCE: 3
MDYAMKSLSL LYPRSLSRHV AVSTAVVTQQ LVSKPSRETP RARPCRVSTA DRKVRKGIMA   60
HSLEDLLNKV QDILKLKDKP FSLVLEEDGT IVETEEYFQA LAKDTMPMVL LKGQKWKPPS  120
EQRKKRAQLA LSQKPTKKID VARVTFDLYK LNPQDFIGCL NVKATLYDTY SLSYDLHCYK  180
AKRIVKEMLR WTLFSMQATG HMLLGTSSYM QQFLDATEEE QPAKAKPSSL LPACLKMLQ   239

SEQ ID NO: 4            moltype = AA   length = 246
FEATURE                 Location/Qualifiers
source                  1..246
                        mol_type = protein
                        organism = Macaca mulatta
SEQUENCE: 4
MGSLRKGFGL LKDPWERAGF DWAACLRVSV RTSVVTQQLL SEPSPEAPRA RPCRVSTADR   60
SVRKGIMAYS LEDLLLKVRD TLMLADKPFF LVLEEDGTTV ETEEYFQALA GDIVFMVLQK  120
GQKWQPPSEQ GTRHPQSLSH KPAKKIDVAR VTFDLYKLNP QDFIGCLNVK ATFYDTYSLS  180
YDLHCCGAKR IVKEALRWAL FSMQATGHVM LGTSCYLQQL LDATEEGQPP KGKASSLIPT  240
CLRILQ                                                             246

SEQ ID NO: 5            moltype = AA   length = 238
FEATURE                 Location/Qualifiers
source                  1..238
                        mol_type = protein
                        organism = Canis lupus familiaris
SEQUENCE: 5
```

```
MEYAMKSLSL LYPKSLSRHV AVSTSVVTQQ LSSKSSLEAP KARPCRVSTA DRSVRKGIIA  60
HSLKDLLNKV RDTLLLADKP FYLVLEEDGT TVETEEYFQA LADDTVFMVL QKGQKWQPPQ 120
EQGSRYQLSL SHKPAKKIDV AQVTFDLYKM NPQDFIGCLN VKATLYGTYS LSYDLHCYGA 180
KRIMKEVLRW ALFSMKTTGH VLLGTSCYMQ QLLDATEGGQ PPEGKARSLI PTSLKMLQ   238

SEQ ID NO: 6            moltype = AA  length = 222
FEATURE                 Location/Qualifiers
source                  1..222
                        mol_type = protein
                        organism = Bos taurus
SEQUENCE: 6
MAMYTAVSTS VVTQQQLSEP SAEAPRARPC RVTTADRSVR KGIMVHSLED LHVKVQDTLM  60
LAYRPFFLVL EEDGTTVETE EYFQSLADDT VFMVLHKGQK WQPPSEQSTR YQLALSHKPA 120
KIDVAQVTFD LYKVNPQDFI GCLNVKATLY GTYSVSYDLH CSGAKRIMKE ALRWALFSMR 180
TTGHMLLGTS CYLQQLLDAT EREQPPKSKA ASLIPTSLKM LQ                    222

SEQ ID NO: 7            moltype = AA  length = 236
FEATURE                 Location/Qualifiers
source                  1..236
                        mol_type = protein
                        organism = Xenopus sp.
SEQUENCE: 7
MEYAMKSLSL LSPKSLTKCV SVSASMTQQL LSRPVSKPRP FRVCNSNRSL RKGIVANSLE  60
DLINKTQDAL LMLEAITLVL DEDGTCVDTE EFFRSLDDGA VFMALAKGQK WKPTENSGYH 120
LSLTKKPARK IDVACVSFDL YKNHPRDFIG CLNVKATLYG TYSLSYDLQC YGAKRMVKEA 180
LRWTLYTMQA TGHVLLGTSC YMKQLLDATE RPVTEEEKSS TTLRDFIPFS PWKMLQ     236
```